US012617810B2

(12) United States Patent
Alibhai et al.

(10) Patent No.: US 12,617,810 B2
(45) **Date of Patent: *May 5, 2026**

(54) PRODRUGS OF STAT3 INHIBITORS

(71) Applicant: Tvardi Operating Company, Inc., Sugar Land, TX (US)

(72) Inventors: Imran Alibhai, Sugar Land, TX (US); Sofia de Achaval, Missouri City, TX (US); Jeffrey Larson, Seabrook, TX (US); Brad Henke, Cary, NC (US)

(73) Assignee: Tvardi Operating Company, Inc., Sugar Land, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/741,674

(22) Filed: Jun. 12, 2024

(65) Prior Publication Data

US 2024/0327438 A1 Oct. 3, 2024

Related U.S. Application Data

(63) Continuation of application No. 18/446,987, filed on Aug. 9, 2023, now Pat. No. 12,043,640, which is a
(Continued)

(51) Int. Cl.

*C07F 9/12* (2006.01)
*C07C 311/29* (2006.01)

(52) U.S. Cl.

CPC .............. *C07F 9/12* (2013.01); *C07C 311/29* (2013.01)

(58) Field of Classification Search

None
See application file for complete search history.

(56) References Cited

U.S. PATENT DOCUMENTS 4,279,909 A 7/1981 Takashima
6,492,428 B1 12/2002 Al-Abed et al.
(Continued)

FOREIGN PATENT DOCUMENTS

CA 2805206 A1 2/2012
WO WO-2006069001 A2 6/2006
(Continued)

OTHER PUBLICATIONS

EurekAlert ("TTUHSC researcher to study new pathway to inhibit protein found in many cancers" New Release, published Dec. 13, 2023, https://www.eurekalert.org/news-releases/1010994) (Year: 2023).*
(Continued)

*Primary Examiner* — Amy C Bonaparte
(74) *Attorney, Agent, or Firm* — Antheros Legal Advisors LLP

(57) ABSTRACT

Provided herein, in certain embodiments, are compounds of Formula I:

(I)

(Continued)

or a pharmaceutically acceptable salt or a solvate thereof, compositions comprising a compounds of Formula I, or a pharmaceutically acceptable salt or a solvate thereof, and uses thereof such as in treating certain diseases or disorders (e.g., cancer, fibrosis, chronic inflammation).

14 Claims, 1 Drawing Sheet

Related U.S. Application Data continuation of application No. PCT/US2023/068240, filed on Jun. 9, 2023.

(60) Provisional application No. 63/366,437, filed on Jun. 15, 2022.

(56) References Cited

U.S. PATENT DOCUMENTS

| | | | | |
|---|---|---|---|---|
| 6,608,101 | B1 | 8/2003 | Ni et al. | |
| 8,779,001 | B2 * | 7/2014 | Tweardy | A61P 1/18 514/604 |
| 8,975,399 | B2 | 3/2015 | Zagury et al. | |
| 10,112,933 | B2 * | 10/2018 | Tweardy | C07D 239/60 |
| 10,676,455 | B2 * | 6/2020 | Tweardy | A61K 31/18 |
| 11,026,905 | B2 | 6/2021 | De Achaval et al. | |
| 11,077,077 | B1 | 8/2021 | Alibhai et al. | |
| 11,161,831 | B2 * | 11/2021 | Tweardy | C07C 323/49 |
| 11,547,683 | B2 | 1/2023 | Alibhai et al. | |
| 11,826,315 | B2 | 11/2023 | De Achaval et al. | |
| 12,043,640 | B2 * | 7/2024 | Alibhai | C07F 9/65744 |
| 12,053,444 | B2 | 8/2024 | Alibhai et al. | |
| 2004/0048795 | A1 | 3/2004 | Ivanova et al. | |
| 2005/0239886 | A1 | 10/2005 | Hamuro et al. | |
| 2005/0287664 | A1 | 12/2005 | Fann | |
| 2006/0148715 | A1 | 7/2006 | Tweardy | |
| 2006/0239990 | A1 | 10/2006 | Nabel et al. | |
| 2007/0004704 | A1 | 1/2007 | Damon et al. | |
| 2007/0203236 | A1 | 8/2007 | Smith et al. | |
| 2009/0221542 | A1 | 9/2009 | Wang et al. | |
| 2009/0326063 | A1 | 12/2009 | Sporn et al. | |
| 2010/0035793 | A1 | 2/2010 | Lim et al. | |
| 2010/0041685 | A1 | 2/2010 | Tweardy et al. | |
| 2010/0209950 | A1 | 8/2010 | Gernez et al. | |
| 2010/0292234 | A1 | 11/2010 | Pettus et al. | |
| 2011/0312984 | A1 | 12/2011 | Tweardy et al. | |
| 2011/0318753 | A1 | 12/2011 | Doi et al. | |
| 2012/0003191 | A1 | 1/2012 | Burkin et al. | |
| 2012/0035163 | A1 | 2/2012 | Yasuma et al. | |
| 2012/0040917 | A1 | 2/2012 | Orum et al. | |
| 2012/0178718 | A1 | 7/2012 | Nique et al. | |
| 2012/0308564 | A1 | 12/2012 | Bayliffe | |
| 2013/0022993 | A1 | 1/2013 | Doi et al. | |
| 2013/0123266 | A1 | 5/2013 | Zagury et al. | |
| 2014/0088171 | A1 | 3/2014 | Yan et al. | |
| 2014/0296270 | A1 | 10/2014 | Tweardy et al. | |
| 2015/0024032 | A1 | 1/2015 | Tweardy et al. | |
| 2015/0031714 | A1 | 1/2015 | Tweardy et al. | |
| 2015/0038443 | A1 | 2/2015 | Li et al. | |
| 2015/0045358 | A1 | 2/2015 | Kao et al. | |
| 2015/0051233 | A1 | 2/2015 | Tweardy et al. | |
| 2018/0009839 | A1 | 1/2018 | Anderson et al. | |
| 2020/0331880 | A1 | 10/2020 | Tweardy et al. | |
| 2021/0038544 | A1 * | 2/2021 | Wied | A61K 31/18 |
| 2021/0114980 | A1 | 4/2021 | Wied et al. | |
| 2021/0228512 | A1 | 7/2021 | Alibhai et al. | |
| 2021/0322347 | A1 | 10/2021 | Alibhai et al. | |
| 2022/0227750 | A1 | 7/2022 | Tweardy et al. | |
| 2023/0077280 | A1 | 3/2023 | Mitch et al. | |
| 2023/0285334 | A1 | 9/2023 | Alibhai et al. | |
| 2024/0018172 | A1 | 1/2024 | Alibhai et al. | |
| 2024/0033234 | A1 | 2/2024 | Alibhai et al. | |
| 2024/0058284 | A1 | 2/2024 | de Achaval et al. | |
| 2025/0170065 | A1 | 5/2025 | Alibhai et al. | |
| 2025/0170079 | A1 | 5/2025 | Alibhai et al. | |

FOREIGN PATENT DOCUMENTS

| | | | |
|---|---|---|---|
| WO | WO-2007136858 | A2 | 11/2007 |
| WO | WO-2009089545 | A1 | 7/2009 |
| WO | WO-2009149192 | A1 | 12/2009 |
| WO | WO-2012017166 | A2 | 2/2012 |
| WO | WO-2012159107 | A1 | 11/2012 |
| WO | WO-2013020372 | A1 | 2/2013 |
| WO | WO-2013078372 | A1 | 5/2013 |
| WO | WO-2013163344 | A1 | 10/2013 |
| WO | WO-2015010102 | A1 | 1/2015 |
| WO | WO-2015010106 | A1 | 1/2015 |
| WO | WO-2015010107 | A1 | 1/2015 |
| WO | WO-2019204427 | A1 | 10/2019 |
| WO | WO-2019204614 | A1 | 10/2019 |
| WO | WO-2021113551 | A1 | 6/2021 |
| WO | WO-2021150912 | A1 | 7/2021 |
| WO | WO-2023168295 | A1 | 9/2023 |
| WO | WO-2023168420 | A1 | 9/2023 |
| WO | WO-2023244946 | A1 | 12/2023 |
| WO | WO-2024020409 | A1 | 1/2024 |
| WO | 2024129619 | A1 | 6/2024 |
| WO | 2025054280 | A1 | 3/2025 |
| WO | 2025137366 | A2 | 6/2025 |

OTHER PUBLICATIONS

Ferriz ("Prodrug Design of Phenolic Drugs" Current Pharmaceutical Design, 2010, p. 2033) (Year: 2010).*

Lipinski ("Experimental and computational approaches to estimate solubility and permeability in drug discovery and development settings" Advanced Drug Delivery Reviews, 2001, p. 3) (Year: 2001).*

Al-Muhsen, S., et al., allergy: an overview, CMAJ, 168(10): 1279-1285 (2003).

Avery, D.T., et al., "STAT3 is required for IL-21-induced secretion of IgE from human naive B cells", Blood, 112(5): 1784-1793 (Sep. 1, 2008).

Bharadwaj, U., et al., Small-molecule inhibition of STAT3 in radioresistant head and neck squamous cell carcinoma, Oncotarget, 7(18): 26307-26330 (2016).

Bonetto, A., et al., STAT3 activation in skeletal muscle links muscle wasting and the acute phase response in cancer cachexia, PLoS One. 6(7): e22538 (2011).

Choi, I-W, et al., TNF-alpha induces the late-phase airway hyper-responsiveness and airway inflammation through cytosolic phospholipase A(2) activation, J Allergy Clin Immunol, 116(3): 537-543 (2005).

Database PubChem Compound [Online] Mar. 26, 2005, retrieved from NCBI, Database accession No. 247699.

Database Registry, Chemical Abstracts Services, CAS Registry No. 36062-33-6 (Entered STN: Nov. 16, 1984).

Database Registry, Chemical Abstracts Services, CAS Registry No. 36062-34-7 (Entered STN: Nov. 16, 1984).

Database Registry, Chemical Abstracts Services, CAS Registry No. 518054-64-3 (Entered STN: May 21, 2003).

Database Registry, Chemical Abstracts Services, CAS Registry No. 518302-64-2 (Entered STN: May 21, 2003).

Database Registry, Chemical Abstracts Services, CAS Registry No. 518302-66-4 (Entered STN: May 21, 2003).

Database Registry, Chemical Abstracts Services, CAS Registry No. 518302-67-5 (Entered STN: May 21, 2003).

Database Registry, Chemical Abstracts Services, CAS Registry No. 518302-68-6 (Entered STN: May 21, 2003).

Database Registry, Chemical Abstracts Services, CAS Registry No. 518302-69-7 (Entered STN: May 21, 2003).

Database Registry, Chemical Abstracts Services, CAS Registry No. 518302-71-1 (Entered STN: May 21, 2003).

Database Registry, Chemical Abstracts Services, CAS Registry No. 518302-73-3 (Entered STN: May 21, 2003).

(56) References Cited

OTHER PUBLICATIONS

Database Registry, Chemical Abstracts Services, CAS Registry No. 518302-74-4 (Entered STN: May 21, 2003).
Database Registry, Chemical Abstracts Services, CAS Registry No. 518302-75-5 (Entered STN: May 21, 2003).
Database Registry, Chemical Abstracts Services, CAS Registry No. 518302-76-6 (Entered STN: May 21, 2003).
Database Registry, Chemical Abstracts Services, CAS Registry No. 518302-77-7 (Entered STN: May 21, 2003).
Database Registry, Chemical Abstracts Services, CAS Registry No. 518302-78-8 (Entered STN: May 21, 2003).
Database Registry, Chemical Abstracts Services, CAS Registry No. 518302-79-9 (Entered STN: May 21, 2003).
Database Registry, Chemical Abstracts Services, CAS Registry No. 518302-80-2 (Entered STN: May 21, 2003).
Database Registry, Chemical Abstracts Services, CAS Registry No. 518302-82-4 (Entered STN: May 21, 2003).
De Castro Barbosa, T., et al., Potential role of growth hormone in impairment of insulin signaling in skeletal muscle, adipose tissue, and liver of rats chronically treated with arginine, Endocrinology, 150(5): 2080-2086 (2009).
Debnath, B., et al., "Small Molecule Inhibitors of Signal Transducer and Activator of Transcription 3 (Stat3) Protein", J. Med. Chem., 55: 6645-6668, (2012).
Fan, D., et al., "Cardic fibroblasts, fibrosis and extracellular matrix remodeling in heart disease", Fibrogenesis & Tissue Repair, 5:15 (2012).
Galli, S.J., et al., The development of allergic inflammation, Nature, 454(7203): 445-454 (2008).
Gavino, A.C., et al., "Small-Molecule Inhibition of STAT3 Prevents House-Dust-Mite (HDM)-Induced Airway Inflammation by Blocking Lung Production of Th17 and Th2 Cytokines", J Allergy Clin Immunol (Feb. 2014).
Hakala, M., "Poor prognosis in patients with rheumatoid arthritis hospitalized for interstitial lung fibrosis", Chest, 93:114-118, (1988).
Kang, N.-I., et al., Tumor necrosis factor-alpha develops late anaphylactic reaction through cytosolic phospholipase A(2) activation, Int Arch Allergy Immunol, 147(4): 315-322 (2008).
Keto-Enol Tautomerism webpage printout retrieved on Aug. 17, 2022 at <https://www.chemistrylearner.com/keto-enol-tautomerism.html>, pp. 1-6 (2022).
Kishimoto, T.K., et al., Contaminated heparin associated with adverse clinical events and activation of the contact system, N Engl J Med, 358(23): 2457-2467 (2008).
Lindsay, K., et al., "Liver fibrosis in patients with psoriasis and psoriatic arthritis on long-term, high cumulative dose methotrexate therapy", Rheumatology, 48:569-572, (2009).
Longley, D.B., et al., 5-fluorouracil: mechanisms of action and clinical strategies, Nat Rev Cancer, 3(5): 330-338 (2003).
Mandal, A., Types of Fibrosis, retrieved from <https://www.news-medical.net/health/Types-of-Fibrosis.aspx>, pp. 1-3 (2019).
Mashili, F., et al., Constitutive STAT3 Phosphorylation Contributes to Skeletal Muscle Insulin Resistance in Type 2 Diabetes, Diabetes, 62(2): 457-465 (2013).
McMurray, J.S., "Structural Basis for the Binding of High Affinity Phosphopeptides to Stat3", PeptideScience, 90(1):69-79, (Nov. 27, 2007).
NIH, Fibrotic Diseases: causes, consequences, prevention, and treatment, pp. 1-2 (2020).
PCT/US2009/046143 International Preliminary Report on Patentability dated Dec. 6, 2010.
PCT/US2009/046143 International Search Report and Written Opinion mailed Nov. 5, 2009.
PCT/US2019/028135 International Search Report and Written Opinion mailed Jul. 5, 2019.
PCT/US2020/063167 International Search Report and Written Opinion mailed Mar. 3, 2021.
PCT/US2021/014642 International Preliminary Report on Patentability dated Jul. 26, 2022.
PCT/US2023/068240 International Search Report and Written Opinion mailed Sep. 27, 2023.
PCT/US2023/070440 International Search Report and Written Opinion mailed Nov. 21, 2023.
Pedroza, M., et al., The Role of STAT-3 in the Development of Pulmonary and Dermal Fibrosis, 2013 ACR/ARHP Annual Meeting, Abstract 2573 (2013).
Priceman, S.J., et al., Regulation of adipose tissue T cell subsets by Stat3 is crucial for diet-induced obesity and insulin resistance, Proc Natl Acad Sci USA, 110(32): 13079-13084 (2013).
Rosenbloom, J., et al., Strategies for anti-fibrotic therapies, Biochim Biophys Acta, 1832(7): 1088-1103 (2013).
Santos Silva, K.A., et al., A new therapeuthical approach to block cancer cachexia: focusing inhibition of STAT3, FASEB J, 27(S1) (2013).
Santos Silva, K.A., et al., Inhibition of Stat3 activation suppresses caspase-3 and the ubiquitin-proteasome system, leading to preservation of muscle mass in cancer cachexia, J Biol Chem, 290(17): 11177-11187 (2015).
Savjani, K.T., et al., Drug solubility: importance and enhancement techniques, ISRN Pharm, 2012:195727, pp. 1-10 (2012).
SelleckChem C188-96 STAT Inhibitor, pp. 1-2 (2013) retrieved on Jan. 9, 2024 from <https://web.archive.org/web/2018004074411/https://www.selleckchem.com/products/c188-9.html>.
Simeone-Penney, M.C., et al., Airway epithelial STAT3 is required for allergic inflammation in a murine model of asthma, J Immunol, 178(10): 6191-6199 (2007).
Tautz, L., et al., Inhibition of Yersinia tyrosine phosphatase by furanyl salicylate compounds, J Biol Chem, 280(10): 9400-9408 (2005).
Titov, E.A., et al., N-Arylsulfonyl-2-(2-hydroxy-1-naththyl)-1,4-naphthoquinoneimines, Ukrainskii Khimicheskii Zhurnal (Russian Edition), 38(1): 73-76 (1972).
U.S. Appl. No. 12/477,583 dated May 23, 2013.
U.S. Appl. No. 12/477,583 dated Nov. 9, 2011.
U.S. Appl. No. 12/477,583 Office Action dated Aug. 30, 2012.
U.S. Appl. No. 14/335,804 Office Action dated May 16, 2017.
U.S. Appl. No. 14/335,804 Office Action dated May 17, 2016.
U.S. Appl. No. 14/335,804 Office Action dated May 7, 2015.
U.S. Appl. No. 14/335,804 Office Action dated Oct. 16, 2015.
U.S. Appl. No. 14/335,829 Office Action dated Apr. 13, 2018.
U.S. Appl. No. 14/335,829 Office Action dated Apr. 26, 2021.
U.S. Appl. No. 14/335,829 Office Action dated Feb. 28, 2020.
U.S. Appl. No. 14/335,829 Office Action dated Jan. 5, 2017.
U.S. Appl. No. 14/335,829 Office Action dated Jan. 8, 2021.
U.S. Appl. No. 14/335,829 Office Action dated Jun. 12, 2015.
U.S. Appl. No. 14/335,829 Office Action dated Jun. 19, 2019.
U.S. Appl. No. 14/335,829 Office Action dated May 10, 2017.
U.S. Appl. No. 14/335,829 Office Action dated May 13, 2016.
U.S. Appl. No. 14/335,829 Office Action dated Nov. 4, 2015.
U.S. Appl. No. 14/335,829 Office Action dated Nov. 7, 2018.
U.S. Appl. No. 14/335,829 Office Action dated Oct. 25, 2019.
U.S. Appl. No. 14/335,829 Office Action dated Sep. 22, 2020.
U.S. Appl. No. 14/335,829 Office Action dated Sep. 28, 2021.
U.S. Appl. No. 14/335,853 Office Action dated Feb. 1, 2016.
U.S. Appl. No. 14/335,853 Office Action dated Feb. 5, 2019.
U.S. Appl. No. 14/335,853 Office Action dated Jul. 9, 2019.
U.S. Appl. No. 14/335,853 Office Action dated Mar. 13, 2017.
U.S. Appl. No. 14/335,853 Office Action dated May 17, 2018.
U.S. Appl. No. 14/335,853 Office Action dated Nov. 29, 2019.
U.S. Appl. No. 14/335,853 Office Action dated Oct. 6, 2017.
U.S. Appl. No. 14/335,853 Office Action dated Sep. 29, 2016.
U.S. Appl. No. 16/848,661 Office Action dated Mar. 11, 2021.
U.S. Appl. No. 17/048,602 Office Action dated Sep. 1, 2022.
U.S. Appl. No. 17/077,821 Pre-Interview Office Action dated Janauary 13, 2021.
White, A.T., et al., Knockout of STAT3 in skeletal muscle does not prevent high-fat diet-induced insulin resistance, Mol Metab, 4(8): 569-575 (2015).
Wiemer, A.J., et al., Prodrugs of phosphonates and phosphates: crossing the membrane barrier, Top Curr Chem, 360: 115-160 (2015).

(56) References Cited

OTHER PUBLICATIONS

Xu, X., et al., Chemical probes that competitively and selectively inhibit Stat3 activation, PLoS One, 4(3): e4783 (2009). .
Zhang, L., et al., IL-6 and serum amyloid A synergy mediates angiotensin II-induced muscle wasting, J Am Soc Nephrol, 20(3): 604-612 (2009).
Zhang, L., et al., Stat3 activation links a C/EBP8 to myostatin pathway to stimulate loss of muscle mass, Cell Metab, 18(3): 368-379 (2013).
Zhang, L., Pharmacological inhibition of myostatin suppresses systemic inflammation and muscle atrophy in mice with chronic kidney disease, FASEB J, 25(5): 1653-1663 (2011).
Zhang, L., Satellite cell dysfunction and impaired IGF-1 signaling cause CKD-induced muscle atrophy, J Am Soc Nephrol, 21(3): 419-427 (2010).
U.S. Appl. No. 17/048,602, filed Oct. 18, 2020, U.S. Pat. No. 11,826,315, Nov. 28, 2023, Issued.
U.S. Appl. No. 17/077,821, filed Oct. 22, 2020, U.S. Pat. No. 11,026,905, Jun. 8, 2021, Issued.
U.S. Appl. No. 18/481,522, filed Oct. 5, 2023, Pending.
U.S. Appl. No. 17/203,639, filed Mar. 16, 2021, U.S. Pat. No. 11,077,077, Aug. 3, 2021, Issued.
U.S. Appl. No. 17/305,009, filed Jun. 29, 2021, U.S. Pat. No. 11,547,683, Jan. 10, 2023, Issued.
U.S. Appl. No. 18/059,270, filed Nov. 28, 2022, Allowed.
U.S. Appl. No. 18/447,040, filed Aug. 9, 2023, Pending.
U.S. Appl. No. 18/446,987, filed Aug. 9, 2023, Allowed.
Thomas, S.S., et al., Molecular mechanisms of insulin resistance in chronic kidney disease, Kidney Int, 88(6): 1233-1239 (2015).
Agosti, P., et al., Emerging metabolic risk factors in hepatocellular carcinoma and their influence on the liver microenvironment, Biochim Biophys Acta Mol Basis Dis, 1864(2): 607-617 (2018).
Jung, K.H., et al., Multifunctional Effects of a Small-Molecule STAT3 Inhibitor on NASH and Hepatocellular Carcinoma in Mice, Clin Cancer Res, 23(18): 5537-5546 (2017).

* cited by examiner

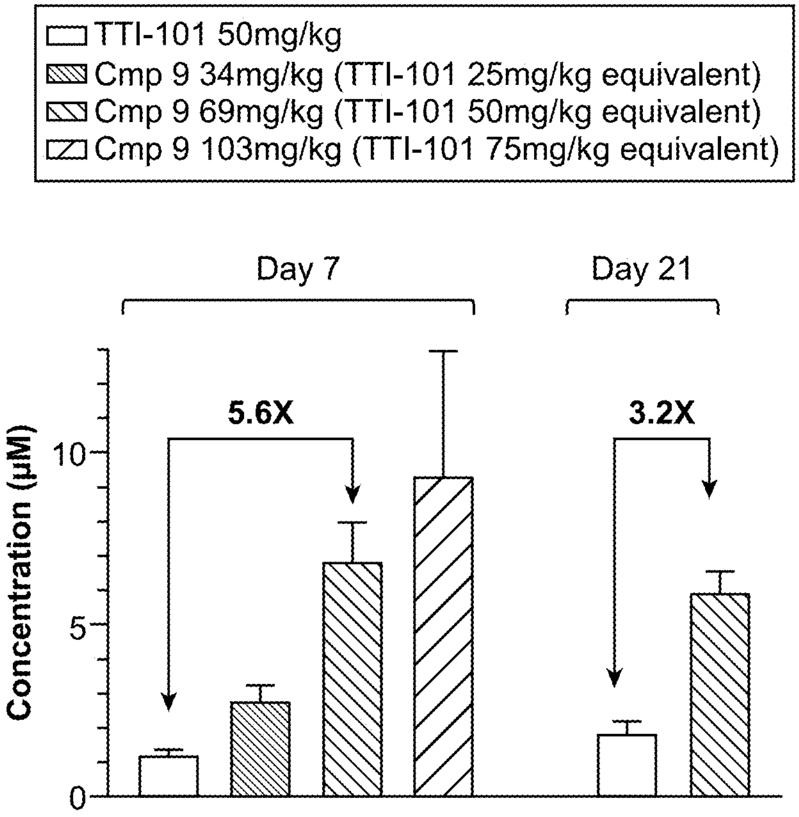
TTI-101 50mg/kg
Cmp 9 34mg/kg (TTI-101 25mg/kg equivalent)
Cmp 9 69mg/kg (TTI-101 50mg/kg equivalent)
Cmp 9 103mg/kg (TTI-101 75mg/kg equivalent)
Day 7
Day 21
5.6X
3.2X
Concentration (μM)
10
5
0

PRODRUGS OF STAT3 INHIBITORS

CROSS REFERENCE

This application is a continuation of U.S. application Ser. No. 18/446,987, filed on Aug. 9, 2023, now issued as U.S. Pat. No. 12,043,640 on Jul. 23, 2024, which is a continuation of International Application No. PCT/US2023/068240, filed Jun. 9, 2023, which claims the benefit of and priority to U.S. Provisional Patent Application No. 63/366,437, filed Jun. 15, 2022, each of which are incorporated herein by reference in their entireties.

SUMMARY

Disclosed herein, in certain embodiments, are compounds of Formula I, or pharmaceutically acceptable salts or solvates thereof, and compositions comprising a compound of Formula I, or a pharmaceutically acceptable salt or a solvate thereof, and a pharmaceutically acceptable carrier. In certain embodiments, the compounds and compositions disclosed herein are effective at inhibiting signal transducer and activator of transcription 3 (STAT3) and thus are useful in methods of treating, preventing, or reducing the risk or severity of certain diseases or disorders such as cancer, fibrosis, and inflammatory diseases or disorders.

In certain embodiments, provided herein is a compound of Formula I:

(I)

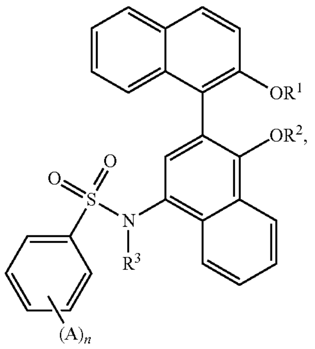

or a pharmaceutically acceptable salt or a solvate thereof, wherein

A is halo, $C_{1-4}$alkyl, $C_{1-4}$alkoxy, $C_{1-4}$haloalkyl, or $C_{1-4}$haloalkoxy;

$R^1$, $R^2$, and $R^3$ are each independently H, C(═O)N$R^AR^B$, P(═O)(OH)($R^C$), or $C_{1-4}$alkylene-O—P(═O)(OH)($R^C$); or $R^1$ and $R^2$ together form:

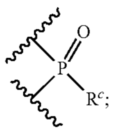

provided that $R^1$, $R^2$ and $R^3$ are not simultaneously H;

$R^A$ is H or $C_{1-4}$alkyl;

$R^B$ is $C_{1-6}$alkylene-N(H)($C_{1-6}$alkyl), $C_{1-6}$alkylene-(5-8 membered heterocyclyl), $C_{1-6}$alkylene-C(═O) OH optionally substituted with amine, $C_{1-4}$alkyl, or benzyl;

$R^C$ is $C_{1-4}$alkyl or hydroxy; and n is an integer 0, 1, 2, or 3.

In certain embodiments, provided herein are pharmaceutical compositions comprising a compound as described herein, or a pharmaceutically acceptable salt or a solvate thereof, and a pharmaceutically acceptable carrier.

In certain embodiments, provided herein are methods that involve the use of (e.g., comprise the administration of) a compound of formula (I), a STAT3 inhibitor, wherein the compound of formula (I) is formulated in a manner described herein (e.g., is present in a composition as described herein). In specific embodiments, provided herein are methods of treating, preventing, or reducing the risk or severity of cancer. In other specific embodiments, provided herein are methods of treating, preventing, or reducing the risk or severity of fibrosis. In still other specific embodiments, provided herein are methods of treating, preventing, or reducing the risk or severity of an inflammatory disease/disorder.

Other objects and advantages will become apparent to those skilled in the art from a consideration of the ensuing Detailed Description, Examples, and Claims.

BRIEF DESCRIPTION OF THE DRAWINGS

The FIGURE shows the comparison of exposures of TTI-101 SEDD and Compound 9 (in PBS) in H22 syngeneic mice.

DETAILED DESCRIPTION

The present disclosure provides, in certain embodiments, compounds of Formula I, (I)

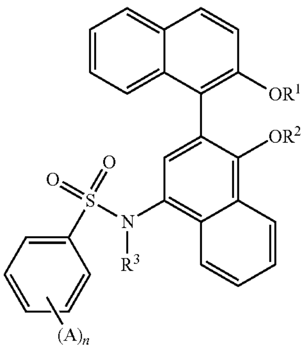

or pharmaceutically acceptable salts or solvates thereof, and compositions comprising a compound of Formula I, or a pharmaceutically acceptable salt or a solvate thereof, and a pharmaceutically acceptable carrier. In certain embodiments, the compounds and compositions disclosed herein are effective at inhibiting signal transducer and activator of transcription 3 (STAT3). Thus, also provided herein, in certain embodiments, are uses of the compounds and compositions in methods of treating, preventing, or reducing the risk or severity of certain diseases or disorders (e.g., cancer, fibrosis, and inflammatory diseases or disorders).

Definitions

The following are definitions of terms used in the present specification. The initial definition provided for a group or term herein applies to that group or term throughout the present specification individually or as part of another group, unless otherwise indicated. Unless otherwise defined, all technical and scientific terms used herein have the same meaning as commonly understood by one of ordinary skill in the art.

As used herein the specification, "a" or "an" may mean one or more. As used herein, when used in conjunction with the word "comprising", the words "a" or "an" may mean one or more than one. As used herein "another" may mean at least a second or more. Still further, the terms "having", "including", "containing" and "comprising" are interchangeable and one of skill in the art is cognizant that these terms are open ended terms. Some embodiments of the invention may consist of or consist essentially of one or more elements, method steps, and/or methods of the invention. It is contemplated that any method, compound, or composition described herein can be implemented with respect to any other method, compound, or composition described herein.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl (Cl), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_5$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., $—CH_3$). In certain embodiments, the alkyl group is substituted $C_{1-10}$ alkyl. Common alkyl abbreviations include Me ($—CH_3$), Et ($—CH_2CH_3$), iPr ($—CH(CH_3)_2$), nPr ($—CH_2CH_2CH_3$), n-Bu ($—CH_2CH_2CH_2CH_3$), or i-Bu ($—CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene ($—CH_2—$), ethylene ($—CH_2CH_2—$), propylene ($—CH_2CH_2CH_2—$), butylene ($—CH_2CH_2CH_2CH_2—$), pentylene ($—CH_2CH_2CH_2CH_2CH_2—$), hexylene ($—CH_2CH_2CH_2CH_2CH_2CH_2—$), and the like. Exemplary substituted alkylene groups, e.g., substituted with one or more alkyl (methyl) groups, include but are not limited to, substituted methylene ($—CH(CH_3)—$, ($—C(CH_3)_2—$), substituted ethylene ($—CH(CH_3)CH_2—$, $—CH_2CH(CH_3)—$, $—C(CH_3)_2CH_2—$, $—CH_2C(CH_3)_2—$), substituted propylene ($—CH(CH_3)CH_2CH_2—$, $—CH_2CH(CH_3)CH_2—$, $—CH_2CH_2CH(CH_3)—$, $—C(CH_3)_2CH_2CH_2—$, $—CH_2C(CH_3)_2CH_2—$, $—CH_2CH_2C(CH_3)_2—$), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Alkoxy" refers to the group-OR' where R' is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, R' is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-$S(O)_2$— and aryl-$S(O)_2$—. Exemplary 'substituted alkoxy' groups include, but are not limited to, —O—$(CH_2)$, ($C_6$-$C_{10}$ aryl), —O—$(CH_2)$, (5-10 membered heteroaryl), —O—$(CH_2)_t$($C_3$-$C_{10}$ cycloalkyl), and —O—$(CH_2)_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —$OCF_3$, —$OCH_2CF_3$, —$OCH_2Ph$, —$OCH_2$-cyclopropyl, —$OCH_2CH_2OH$, and —$OCH_2CH_2NMe_2$.

"Amino" or "amine" refers to the radical —$NH_2$.

"Oxo group" refers to —C(═O)—. "Carboxy" refers to the radical —C(O)OH.

"Halo" or "halogen" refers to fluoro (F), chloro (Cl), bromo (Br), and iodo (I). In certain embodiments, the halo group is either fluoro or chloro.

"Haloalkyl" refers to an alkyl radical in which the alkyl group is substituted with one or more halogens. Typical haloalkyl groups include, but are not limited to, trifluoromethyl, difluoromethyl, fluoromethyl, chloromethyl, dichloromethyl, dibromoethyl, tribromomethyl, tetrafluoroethyl, and the like.

"Haloalkoxy" refers to an alkoxy radical in which the alkyl group is substituted with one or more halogens. Typical haloalkoxy groups include, but are not limited to, trifluoromethoxy, difluoromethoxy, fluoromethoxy, chloromethoxy, dichloromethoxy, dibromoethoxy, tribromomethoxy, tetrafluoroethoxy, and the like.

"Hydroxy" refers to the radical —OH.

"Benzyl" refers to the radical —$CH_2$—$C_6H_5$ and which may be substituted or unsubstituted.

Unless otherwise indicated, any heteroatom with unsatisfied valences is assumed to have hydrogen atoms sufficient to satisfy the valences.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic, substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Certain compounds of the present disclosure may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this disclosure.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the International Union of Pure and Applied Chemistry (IUPAC) 1974 Recommendations. The racemic forms can be resolved by physical methods, such as, for example, fractional crystallization, separation or crystallization of diastereomeric derivatives, or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present disclosure are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Isomeric mixtures containing any of a variety of isomer ratios may be utilized in accordance with the present disclosure. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present disclosure. Those of ordinary skill in the art will readily appreciate that analogous ratios are contemplated for more complex isomer mixtures.

The present disclosure also includes isotopically-labeled compounds, which are identical to the compounds disclosed herein, but for the fact that one or more atoms are replaced by an atom having an atomic mass or mass number different from the atomic mass or mass number usually found in nature. Examples of isotopes that can be incorporated into compounds of the present disclosure include isotopes of hydrogen, carbon, nitrogen, oxygen, phosphorous, sulfur, fluorine, and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present disclosure, or an enantiomer, diastereomer, tautomer, or pharmaceutically acceptable salt or solvate thereof, which contain the aforementioned isotopes and/or other isotopes of other atoms are within the scope of this invention. Certain isotopically-labeled compounds of the present disclosure, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and hence, may be preferred in some circumstances. Isotopically labeled compounds can generally be prepared by carrying out the procedures disclosed in the Schemes and/or in the Examples below, by substituting a readily-available isotopically labeled reagent for a non-isotopically labeled reagent.

If, for instance, a particular enantiomer of a compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically active acid or base, followed by resolution of the diastereomers thus formed by fractional crystallization or chromatographic means well known in the art, and subsequent recovery of the pure enantiomers.

Compounds of the present disclosure are, subsequent to their preparation, preferably isolated and purified to obtain a composition containing an amount by weight equal to or greater than 90%, for example, equal to greater than 95%, equal to or greater than 99% of the compounds ("substantially pure" compounds), which is then used or formulated as described herein. Such "substantially pure" compounds of the present invention are also contemplated herein as part of the present invention.

As used herein, "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^{+}(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, "solvate" refers to a physical association of a compound with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvate may comprise either a stoichiometric or nonstoichiometric amount of the solvent molecules. For example, a solvate with a nonstoichiometric amount of solvent molecules may result from partial loss of solvent from the solvate. "Solvate" encompasses both solution-phase and isolable solvates. Exemplary solvates include, but are not limited to, hydrates, ethanolates, methanolates, isopropanolates and the like.

As used herein, "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As used herein, a "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In some embodiments, the subject is a human. In some embodiments, the subject is a non-human animal. The terms "human," "patient," "subject," and "individual" are used interchangeably herein. None of these terms require the active supervision of medical personnel.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or reverses or slows the progression of the disease, disorder or condition (also "therapeutic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject. A "therapeutically effective amount" of a compound is an amount sufficient to provide a therapeutic benefit (e.g., treating, preventing, and/or ameliorating cancer in a subject, or inhibiting protein-protein interactions mediated by an SH2 domain in a subject, at a reasonable benefit/risk ratio applicable to any medical treatment) in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent. A "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent. A "prophylactic treatment" contemplates an action that occurs before a subject begins to suffer from the specified disease, disorder or condition.

As used herein, "STAT3 inhibitor" or a compound that "inhibits STAT3" refers to a compound that interferes with the activity of STAT3 to perform one or more activities, including the ability of STAT3 to bind to a molecule such as pY-peptide ligand and/or the ability to be phosphorylated.

"TTI-101" as used herein refers to a compound with the following structure:

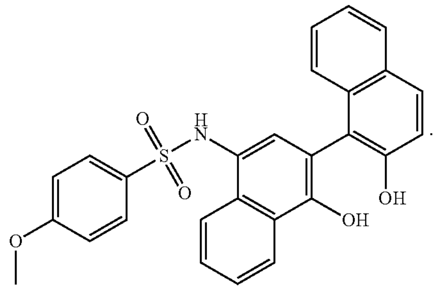 [SMILES: COc1ccc(S(=O)(=O)Nc2cc(-c3c(O)ccc4ccccc34)c(O)c3ccccc23)cc1]

Compounds

TTI-101 is highly insoluble ("brick dust"). It is insoluble in aqueous solutions and has relatively low solubility in most solvents. Furthermore, it has a crystalline structure with high crystal-lattice energy, contributing to rapid precipitation or crystallization of the compound from solution. Its low solubility and high crystallinity have contributed to various difficulties in preparing formulations that are suitable for administration in human subjects.

Disclosed herein, in certain embodiments, are compounds of Formula I that provide high solubility (e.g., in an aqueous solution) and stability at multiple pHs and exhibit improved chemical stabilization while maintaining comparable pharmacokinetic properties as TTI-101. In some embodiments, the compounds of Formula I have significantly improved chemical stabilization relative to that are ester (—O—C(O)) or carbonate (—O—C(O)—O—) based compounds of TTI-101.

In certain embodiments, provided herein is a compound of Formula I:

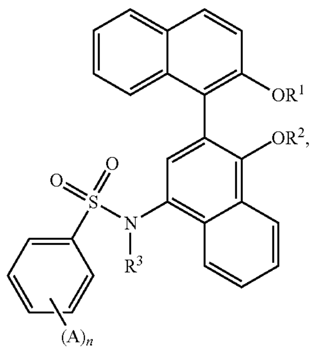

(I)

or a pharmaceutically acceptable salt or a solvate thereof, wherein

A is halo, $C_{1-4}$alkyl, $C_{1-4}$alkoxy, $C_{1-4}$haloalkyl, or $C_{1-4}$haloalkoxy;

$R^1$, $R^2$, and $R^3$ are each independently H, C(=O)$NR^AR^B$, P(=O)(OH)($R^C$), or $C_{1-4}$alkylene-O—P(=O)(OH)($R^C$); or $R^1$ and $R^2$ together form:

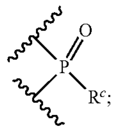

provided that $R^1$, $R^2$ and $R^3$ are not simultaneously H;

$R^A$ is H or $C_{1-4}$alkyl;

$R^B$ is $C_{1-6}$alkylene-N(H)($C_{1-6}$alkyl), $C_{1-6}$alkylene-(5-8 membered heterocyclyl), $C_{1-6}$alkylene-C(=O) OH optionally substituted with amine, $C_{1-4}$alkyl, or benzyl;

$R^C$ is $C_{1-4}$alkyl or hydroxy; and n is an integer 0, 1, 2, or 3.

In certain embodiments, $R^3$ is H. In other embodiments, $R^3$ is C(=O)$NR^AR^B$. In certain embodiments, $R^3$ is P(=O)(OH)($R^c$). In certain embodiments, $R^3$ is $C_{1-4}$alkylene-O—P(=O)(OH)($R^c$). In certain embodiments, $R^3$ is H or C(=O)$NR^AR^B$. In certain embodiments, $R^3$ is H or C(=O)$NR^AR^B$ wherein $R^A$ is H and $R^B$ is $C_{1-6}$alkylene-C(=O) OH optionally substituted with amine.

In certain embodiments, $R^1$ is H. In other embodiments, $R^1$ is C(=O)$NR^AR^B$. In certain embodiments, $R^1$ is P(=O)(OH)($R^c$). In certain embodiments, $R^1$ is $C_{1-4}$alkylene-O—P(=O)(OH)($R^c$). In certain embodiments, $R^1$ is H, C(=O)$NR^AR^B$, or P(=O)(OH)($R^c$). In certain embodiments, $R^1$ is H, C(=O)$NR^AR^B$ wherein $R^A$ is H or methyl and $R^B$ is $C_{1-6}$alkylene-N(H)($C_{1-4}$alkyl), $C_{1-6}$alkylene-C(=O) OH optionally substituted with amine, or $C_{1-6}$alkylene-(5-6 membered heterocyclyl), or P(=O)$(OH)_2$. In certain embodiments, $R^1$ is H, C(=O)$NR^AR^B$ wherein $R^A$ is H or methyl and $R^B$ is $C_{26}$alkylene-N(H)($C_{1-4}$alkyl), $C_{2-6}$alkylene-C(=O) OH optionally substituted with amine, or $C_{2-6}$alkylene-(5-membered heterocyclyl), or P(=O)$(OH)_2$.

In certain embodiments, $R^2$ is H. In other embodiments, $R^2$ is C(=O)$NR^AR^B$. In certain embodiments, $R^2$ is P(=O)(OH)($R^c$). In certain embodiments, $R^2$ is $C_{1-4}$alkylene-O—P(=O)(OH)($R^c$). In certain embodiments, $R^2$ is H, C(=O)$NR^AR^B$, or P(=O)(OH)($R^c$). In certain embodiments, $R^2$ is H, C(=O)$NR^AR^B$ wherein $R^A$ is H or methyl and $R^B$ is $C_{1-6}$alkylene-N(H)($C_{1-4}$alkyl), $C_{1-6}$alkylene-C(=O) OH optionally substituted with amine, or $C_{1-6}$alkylene-(5-6 membered heterocyclyl), or P(=O)$(OH)_2$. In certain embodiments, $R^2$ is H, C(=O)$NR^AR^B$ wherein $R^A$ is H or methyl and $R^B$ is $C_{2-6}$alkylene-N(H)($C_{1-4}$alkyl), $C_{2-6}$alkylene-C(=O) OH optionally substituted with amine, or $C_{2-6}$alkylene-(5-membered heterocyclyl), or P(=O)$(OH)_2$.

In certain embodiments, $R^1$ and $R^2$ together form:

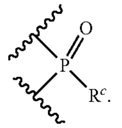

In certain embodiments, $R^1$ and $R^2$ together form:

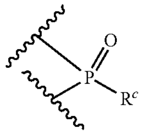

wherein $R^C$ is OH.

In certain embodiments, $R^A$ is H or methyl. In certain embodiments, $R^A$ is H. In certain embodiments, $R^A$ is methyl.

In certain embodiments, $R^B$ is $C_{1-6}$alkylene-N(H)($C_{1-6}$alkyl). In certain embodiments, $R^B$ is $C_{1-4}$alkylene-N(H)($C_{1-6}$alkyl). In certain embodiments, $R^B$ is $C_{24}$alkylene-N(H)($C_{1-6}$alkyl). In certain embodiments, $R^B$ is $CH_2CH_2N(H)$($C_{1-6}$alkyl). In certain embodiments, $R^B$ is $CH_2CH_2CH_2N(H)$($C_{1-6}$alkyl). In certain embodiments, $R^B$ is $CH_2CH_2N(H)(CH_3)$. In certain embodiments, $R^B$ is $CH_2CH_2CH_2N(H)(CH_3)$.

In certain embodiments, $R^B$ is $C_{1-6}$alkylene-(5-8 membered heterocyclyl). In certain embodiments, $R^B$ is $C_{1-4}$alkylene-(5-8 membered heterocyclyl). In certain embodiments, $R^B$ is $C_{1-2}$alkylene-(5-8 membered heterocyclyl). In certain embodiments, $R^B$ is $C_{1-6}$alkylene-(5-8 membered heterocyclyl). In certain embodiments, $R^B$ is $C_{1-4}$alkylene-(5-6 membered heterocyclyl). In certain embodiments, $R^B$ is $C_{1-2}$alkylene-(5-6 membered heterocyclyl). In certain embodiments, $R^B$ is $C_{1-6}$alkylene-(5-membered heterocyclyl). In certain embodiments, $R^B$ is $C_{1-4}$alkylene-(5-membered heterocyclyl). In certain embodiments, $R^B$ is $C_{1-2}$alkylene-(5-membered heterocyclyl). In certain embodiments, $R^B$ is $C_{1-4}$alkylene-(5-8 membered N-containing heterocyclyl). In certain embodiments, $R^B$ is $C_{1-4}$alkylene-(5-6 membered N-containing heterocyclyl). In certain embodiments, $R^B$ is $C_{1-4}$alkylene-(5-membered N-containing heterocyclyl). In certain embodiments, $R^B$ is $C_{1-2}$alkylene-(5-membered heterocyclyl). In certain embodiments, $R^B$ is $C_{1-2}$alkylene-(5-8 membered N-containing heterocyclyl). In certain embodiments, $R^B$ is $C_{1-2}$alkylene-(5-6 membered N-containing heterocyclyl). In certain embodiments, $R^B$ is $C_{1-2}$alkylene-(5-membered N-containing heterocyclyl).

In certain embodiments, $R^B$ is $C_{1-6}$alkylene-C(=O) OH optionally substituted with amine, $C_{1-4}$alkyl, or benzyl. In certain embodiments, $R^B$ is $C_{1-6}$alkylene-C(=O) OH substituted with amine. In certain embodiments, $R^B$ is $C_{1-4}$alkylene-C(=O) OH substituted with amine. In certain embodiments, $R^B$ is $C_{2-6}$alkylene-C(═O) OH substituted with amine. In certain embodiments, $R^B$ is $C_{2-4}$alkylene-C (═O) OH substituted with amine.

In certain embodiments, $R^C$ is $C_{1-4}$alkyl. In some embodiments, $R^C$ is methyl. In other embodiments, $R^C$ is hydroxy.

In certain embodiments, A is halo, $C_{1-4}$alkyl, $C_{1-4}$alkoxy, $C_{1-4}$haloalkyl, or $C_{1-4}$haloalkoxy. In certain embodiments, A is halo, $C_{1-4}$alkyl, or $C_{1-4}$alkoxy. In certain embodiments, A is $C_{1-4}$alkoxy. In certain embodiments, A is methoxy.

In certain embodiments, n is 0, 1, or 2. In certain embodiments, n is 0 or 1. In certain embodiments, n is 0. In certain embodiments, n is 1. In certain embodiments, n is 2.

In certain embodiments, the compound is a compound of Formula I-A:

(I-A)

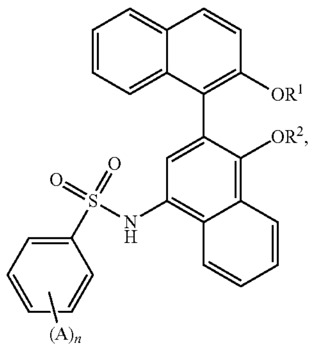

or a pharmaceutically acceptable salt or a solvate thereof.

In certain embodiments, the compound is a compound of Formula I-B:

(I-B)

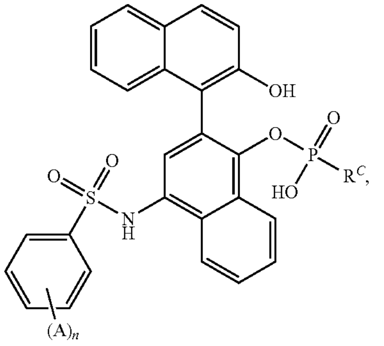

or a pharmaceutically acceptable salt or a solvate thereof.

In certain embodiments, the compound is a compound of Formula I-C:

(I-C)

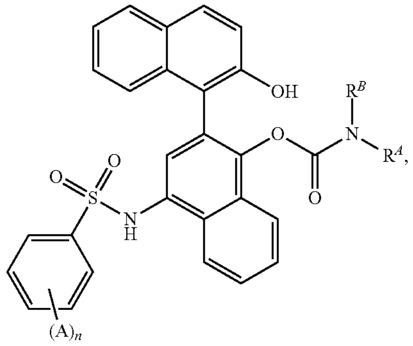

or a pharmaceutically acceptable salt or a solvate thereof.

In certain embodiments, the compound is a compound of Formula I-D:

(I-D)

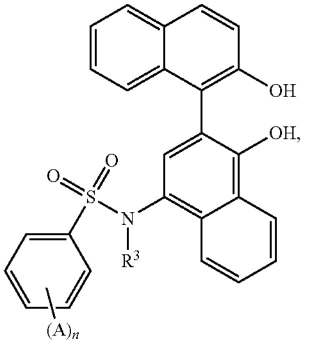

or a pharmaceutically acceptable salt or a solvate thereof.

In certain embodiments, the compound is a compound of Formula I-E:

(I-E)

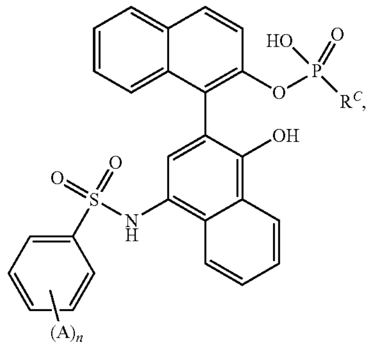

or a pharmaceutically acceptable salt or a solvate thereof.

In certain embodiments, the compound is a compound of Formula I-F:

(I-F)

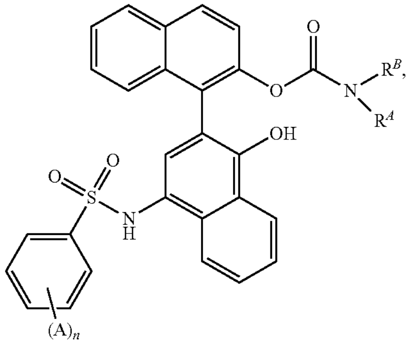

or a pharmaceutically acceptable salt or a solvate thereof.

In certain embodiments, the compound is a compound of Formula I-G:

(I-G)

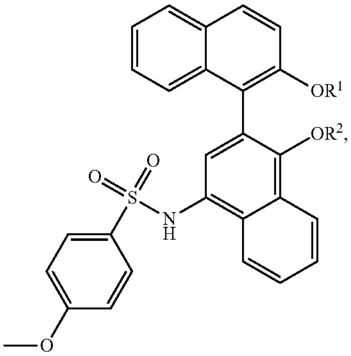

or a pharmaceutically acceptable salt or a solvate thereof.

In certain embodiments, the compound is a compound of Formula I-H:

(I-H)

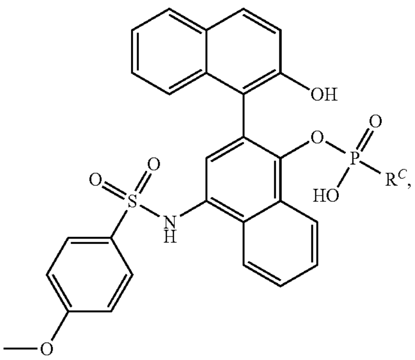

or a pharmaceutically acceptable salt or a solvate thereof.

In certain embodiments, the compound is a compound of Formula I-I:

(I-I)

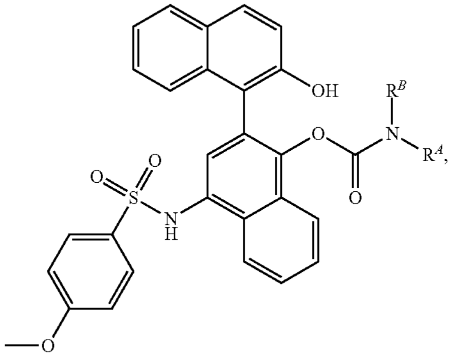

or a pharmaceutically acceptable salt or a solvate thereof.

In certain embodiments, the compound is a compound of Formula I-J:

(I-J)

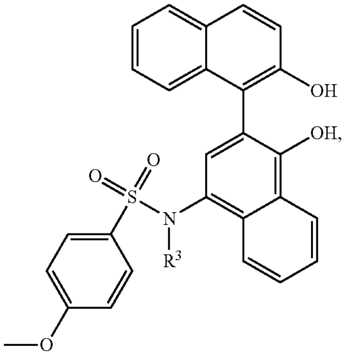

or a pharmaceutically acceptable salt or a solvate thereof.

In certain embodiments, the compound is a compound of Formula I-K:

(I-K)

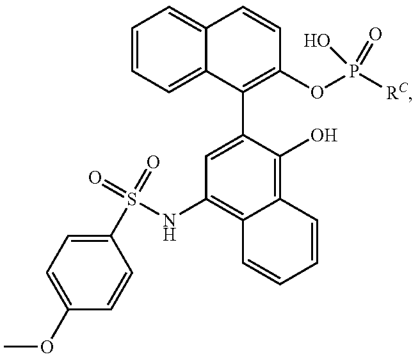

or a pharmaceutically acceptable salt or a solvate thereof.

In certain embodiments, the compound is a compound of Formula I-L:

(I-L)
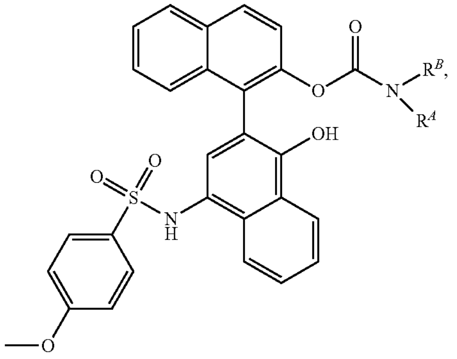
or a pharmaceutically acceptable salt or a solvate thereof.
In certain embodiments, the compound is:
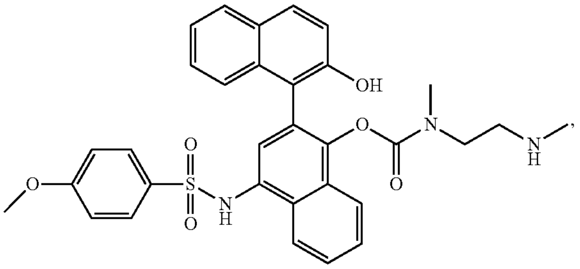
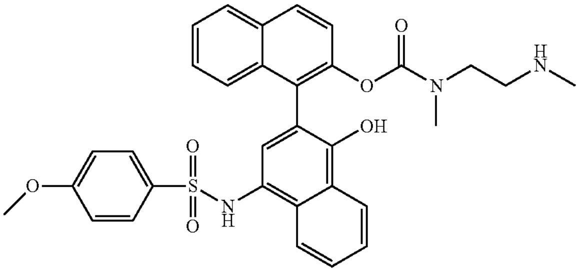
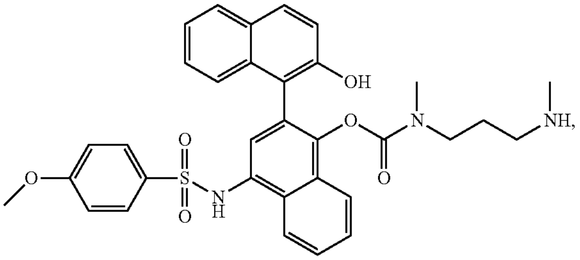
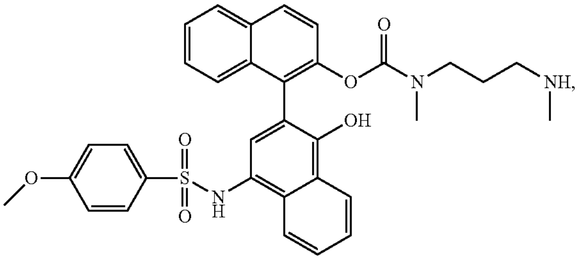
-continued
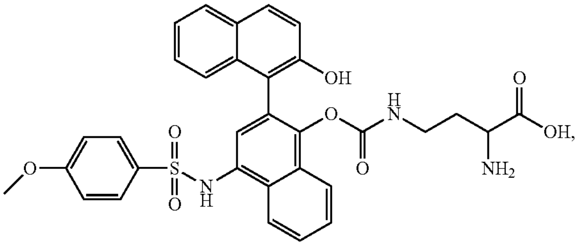
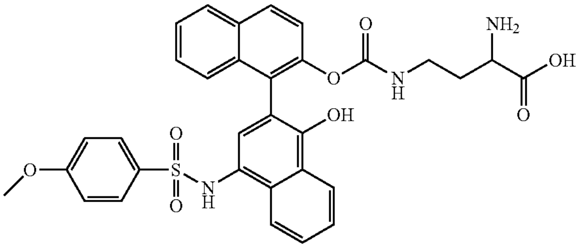
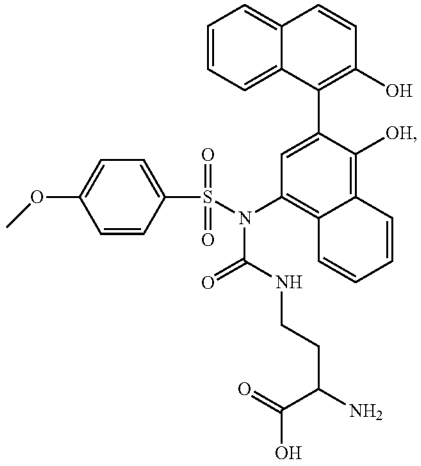
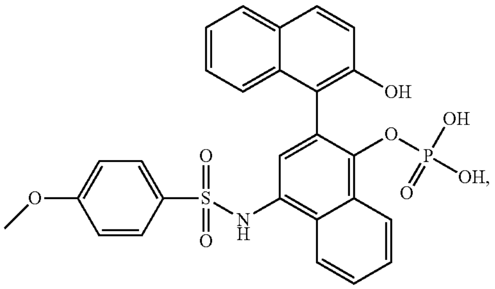
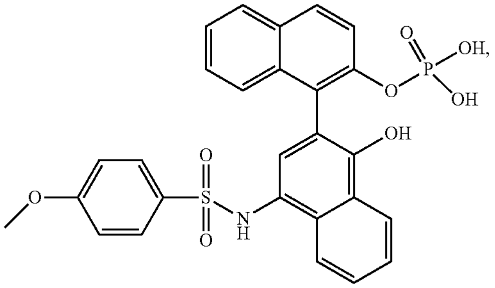

-continued
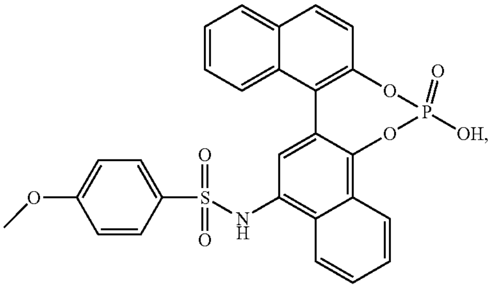
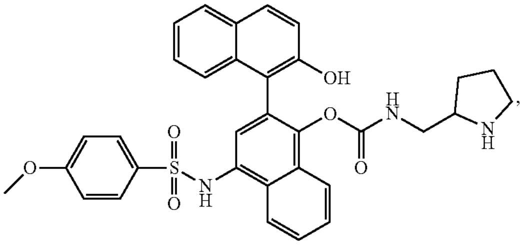
or
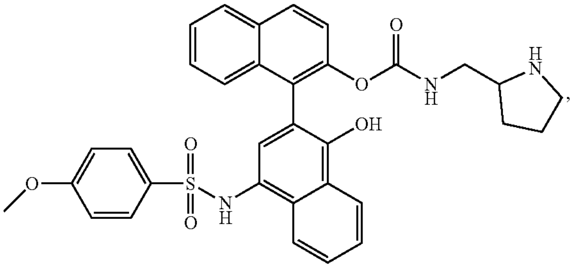
or pharmaceutically acceptable salts or solvates thereof.
In certain embodiments, the compound is:
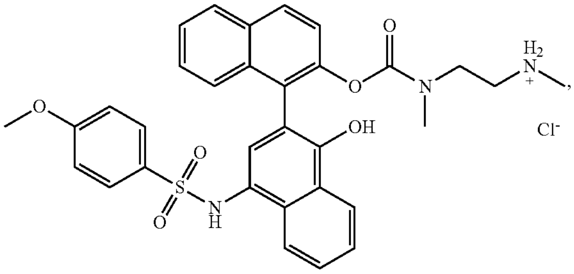
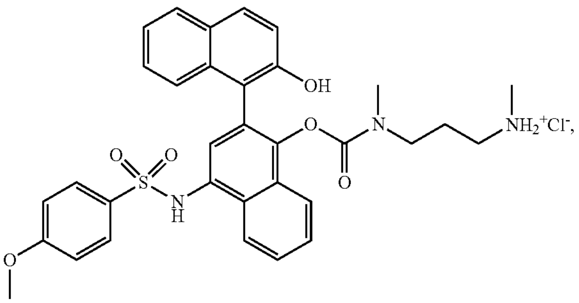
-continued
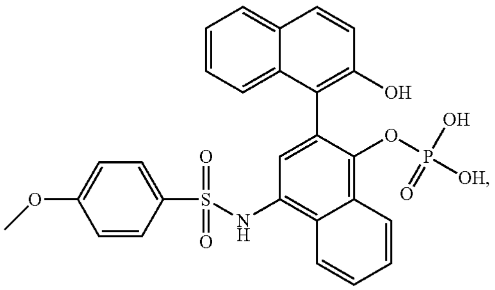
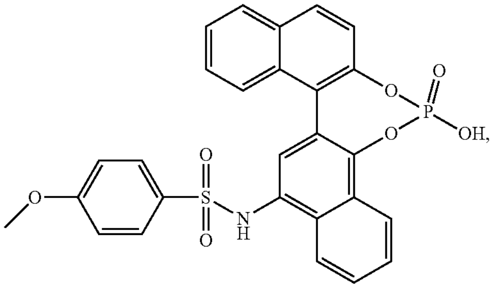
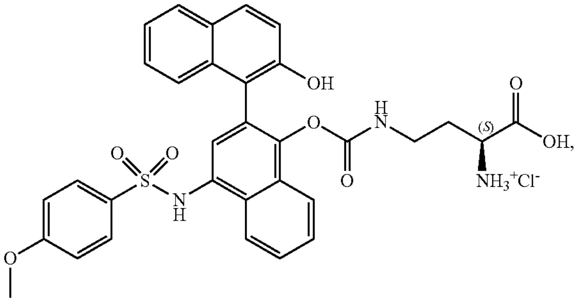
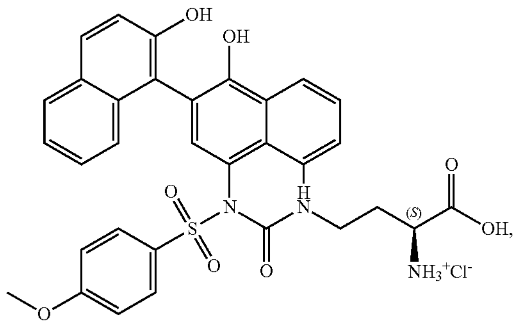
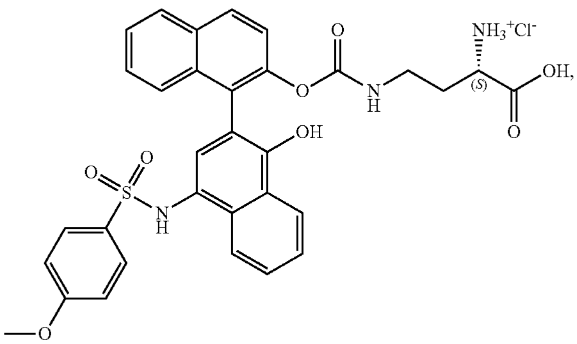

-continued

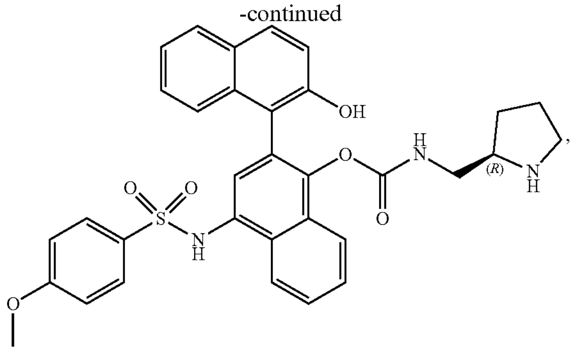

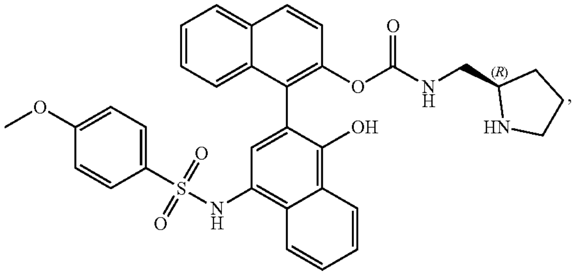

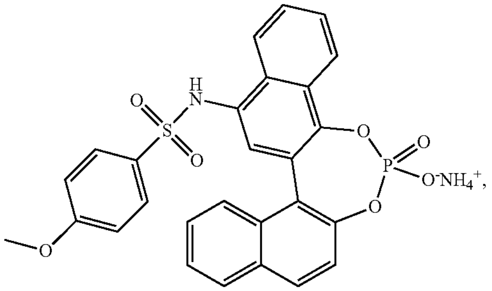

or

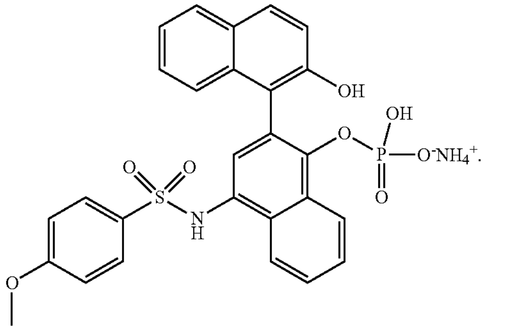

Pharmaceutical Compositions, Administration, and Dosages

In certain embodiments, provided herein are pharmaceutical compositions comprising a compound as described herein, or a pharmaceutically acceptable salt or a solvate thereof, and a pharmaceutically acceptable carrier.

This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 1000 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In some embodiments, compositions comprising a compound of Formula I are administered to the subject as oral dosage forms. In some embodiments, the oral dosage form is in the form of a tablet. In some embodiments, the oral dosage form is in the form of a capsule.

The dosage may vary depending upon the dosage form employed and the route of administration utilized. The exact formulation, route of administration and dosage can be chosen by the individual physician in view of the patient's condition. (See e.g., Fingl, et al., 1975, in 'he Pharmacological Basis of Therapeutics"). Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician. A course of therapy can comprise one or more separate administrations of a compound as described herein.

Methods of Use

Compounds and compositions described herein are utilized in methods for treating, preventing, or reducing the risk or severity of a disease or disorder mediated by STAT3, or a disease or disorder that is otherwise treatable with a STAT3 inhibitor. For example, the compounds and compositions are useful for treating, preventing, or reducing the risk or severity of certain diseases or disorders characterized by excessive STAT3 protein expression. Such diseases and disorders include certain cancers, fibrosis, and inflammatory diseases/disorders.

In some embodiments, the methods involve the use of (e.g., comprise the administration of) a compound of formula (I), a STAT3 inhibitor, wherein the compound of formula (I) is formulated in a manner described herein (e.g., is present in a composition as described herein). In specific embodiments, provided herein are methods of treating, preventing, or reducing the risk or severity of cancer. In other specific embodiments, provided herein are methods of treating, preventing, or reducing the risk or severity of fibrosis. In still other specific embodiments, provided herein are methods of treating, preventing, or reducing the risk or severity of an inflammatory disease/disorder.

Signal transducer and activator of transcription 3 (STAT3) is central in regulating the anti-tumor immune response. STAT3 is broadly hyperactivated both in cancer and non-cancerous cells within the tumor ecosystem and plays important roles in inhibiting the expression of crucial immune activation regulators and promoting the production of immunosuppressive factors. Methods provided herein are contemplated as being useful for the treatment of a cancer, including for example, solid tumors, soft tissue tumors, and metastases thereof.

Provided in certain embodiments herein are methods of treating, preventing, or reducing the risk or severity of a cancer in an individual in need thereof, the method comprising administering to the individual a compound or composition described herein. In some embodiments, the cancer treated according to a method provided herein is a liver cancer, lung cancer, head and neck cancer, breast cancer, skin cancer, kidney cancer, testicular cancer, colon cancer, rectal cancer, gastric cancer, skin cancer, metastatic melanoma, prostate cancer, ovarian cancer, cervical cancer, bone cancer, spleen cancer, gall bladder cancer, brain cancer, pancreatic cancer, stomach cancer, anal cancer, prostate cancer, multiple myeloma, post-transplant lymphoproliferative disease, restenosis, myelodysplastic syndrome, leukemia, lymphoma, or acute myelogenous leukemia. In some embodiments, a cancer treated according to a method provided herein is a liver cancer, lung cancer, liver carcinoma, hepatocellular carcinoma, head and neck squamous cell carcinoma, non-small cell lung cancer, or estrogen receptor-positive breast cancer. In some embodiments, a cancer treated according to a method provided herein is head and neck cancer, lung cancer, liver cancer, breast cancer, ovarian cancer, colon cancer, multiple myeloma, leukemia, or pancreatic cancer. In some embodiments, the leukemia is acute myelogenous leukemia.

Moreover, STAT3 is essential for Th 17 lymphocyte development and cytokine production, and its activation has been linked to the development of airway inflammation. Upon activation, STAT3 is recruited to cytokine-activated receptor complexes and becomes phosphorylated at Tyr (Y) 705. Phosphotyrosylated (p) STAT3 homodimerizes through reciprocal SH2-pY705 interactions, translocates to the nucleus, and binds to promoters to transcriptionally activate genes that drive Th17 differentiation and production of multiple cytokines. STAT3 activation also is involved in Th2 cytokine production, making it an attractive target for asthma treatment. In addition, several genes have been implicated as risk factors for inflammatory bowel disease (IBD) in genome-wide association studies (GWAS), including ATG16L, NOD2/CARD15, IBD5, CTLA4, TNFSF15, JAK2, STAT3, IL23R, and ORMDL3, which implicate antimicrobial peptides, innate and adaptive immune cell function, Th17 cells, regulatory T cells (Tregs), and cytokines (tumor necrosis factor, interleukins 17, 23, 12, 22, and IL-6). Many of these cytokines serve as ligands for cell surface receptors that activate STAT3. STAT3 within three cell lineages-myeloid cells, enterocytes, and T cells—has been demonstrated to contribute to colitis in mice and humans. Thus, targeting STAT3 may represent an effective means of treating, preventing, or reducing the risk or severity of inflammatory disease/disorder.

Provided in certain embodiments herein are methods of treating, preventing, or reducing the risk or severity of an inflammatory disease/disorder in an individual in need thereof, the method comprising administering to the individual a compound or composition described herein. In some embodiments, the inflammatory disease/disorder treated herein is inflammatory bowel disease (IBD), ulcerative colitis, Crohn's disease, asthma, anaphylaxis, cancer cachexia, chronic kidney disease cachexia, nonalcoholic steatohepatitis (NASH), psoriasis, uveitis, scleritis, multiple sclerosis, or pancreatitis. In some embodiments, inflammation treated herein is inflammatory bowel disease (IBD), ulcerative colitis, Crohn's disease, asthma, anaphylaxis, cancer cachexia, chronic kidney disease cachexia, or non-alcoholic steatohepatitis (NASH). In some embodiments, the anaphylaxis comprises anaphylactic shock.

Fibrosis is a pathological process involving the accumulation of excessive extra-cellular matrix in tissues, leading to tissue damage and organ dysfunction, which can progress to organ failure and death. In systemic sclerosis, an idiopathic fibrosis disease, the trigger is postulated to be an autoimmune response that leads to tissue injury, production of growth factors, pro-inflammatory and pro-fibrotic cytokines, and accumulation of myofibroblasts. Two potential sources of myofibroblasts are the differentiation of local fibroblasts and the process of epithelial-to-mesenchymal transition (EMT). IL-6 is a proinflammatory and profibrotic cytokine increasingly recognized as an important mediator of fibrosis that may contribute to the accumulation of myofibroblasts. After engaging its receptor, IL-6 signals through the STAT3. Thus, STAT3 represents a potentially important protein to target to treat fibrosis.

Provided in certain embodiments herein are methods of treating, preventing, or reducing the risk or severity of fibrosis in an individual in need thereof, the method comprising administering to the individual a compound or composition described herein. In certain embodiments, the fibrosis is associated with a disorder or disease such as skin fibrosis (or dermal fibrosis), cardiac fibrosis, cirrhosis, pulmonary fibrosis, bone marrow fibrosis, intestine fibrosis, pancreatic fibrosis, joint fibrosis, liver fibrosis, retroperitoneum, renal fibrosis, myelofibrosis, non-alcoholic fatty liver disease, steatohepatitis, systemic sclerosis (including diffuse systemic sclerosis or limited systemic sclerosis), endomyocardial fibrosis, myocardial infarction, atrial fibrosis, mediastinal fibrosis, progressive massive fibrosis, nephrogenic systemic fibrosis, Keloid, arthrofibrosis, adhesive capsulitis, or cystic fibrosis. In certain embodiments, the fibrosis is associated with skin fibrosis (scleroderma), cardiac fibrosis, cirrhosis, pulmonary fibrosis, bone marrow fibrosis, intestine fibrosis, pancreatic fibrosis, joint fibrosis, liver fibrosis, retroperitoneum, myelofibrosis, non-alcoholic fatty liver disease, steatohepatitis, or systemic sclerosis. In certain embodiments, the fibrosis is associated with skin fibrosis (scleroderma), cardiac fibrosis, cirrhosis, or pulmonary fibrosis.

In certain embodiments, the fibrosis is associated with exposure to certain drugs such as chemotherapy, fibrosis following exposure to environmental or other toxins or allergens, fibrosis occurring after an ischemia/reperfusion injury such as myocardial infarction or hypotension, fibrosis occurring after radiation, fibrosis following hepatitis induced by alcohol, toxins, drugs or infections, primary biliary cirrhosis, fibrosis following viral infections involving the heart, liver, or lung, and/or idiopathic retroperitoneal fibrosis.

Muscle wasting is a debilitating complication of catabolic conditions including chronic kidney disease (CKD), diabetes, cancer, or serious infections. For example, in mice with CKD, inhibition of myostatin reduced circulating levels of IL-6 and TNFα, suggesting a link between inflammation and muscle wasting as reported in clinical studies. STAT3 was found to be activated by the IL-6 family of cytokines, thus suggesting that the STAT3 pathway is linked to loss of muscle mass.

Provided in certain embodiments herein are methods of treating, preventing, or reducing the risk or severity of a muscle wasting disease/disorder, muscle weakness disease/disorder, or cachexia in an individual in need thereof, the method comprising administering to the individual a compound or composition described herein. The muscle weakness and/or muscle wasting and/or cachexia may have an unknown cause or it may be associated with an underlying condition. The underlying condition may be a catabolic condition. In some embodiments, the underlying medical condition associated with cachexia is least renal disease or failure, cancer, AIDS, HIV infection, chronic obstructive lung disease (including emphysema), multiple sclerosis, congestive heart failure, tuberculosis, familial amyloid polyneuropathy, acrodynia, hormonal deficiency, metabolic acidosis, infectious disease, chronic pancreatitis, autoimmune disorder, celiac disease, Crohn's disease, electrolyte imbalance, Addison's disease, sepsis, burns, trauma, fever, long bone fracture, hyperthyroidism, prolonged steroid therapy, surgery, bone marrow transplant, atypical pneumonia, brucellosis, endocarditis, Hepatitis B, lung abscess, mastocytosis, paraneoplastic syndrome, polyarteritis nodosa, sarcoidosis, systemic lupus erythematosus, myositis, polymyositis, dematomyosytis, rheumatological diseases, autoimmune disease, collagen-vascular disease, visceral leishmaniasis, prolonged bed rest, and/or addiction to drugs, such as amphetamine, opiates, or barbitutates.

In addition, STAT3 signaling has been implicated in gap junction intercellular communication, IL-6- and IL11-induced vascular leakage, down-regulation of VE-cadherin concomitant with phosphorylation of STAT3, and the STAT3/mir17-92/E2F1 dependent regulation of β-catenin nuclear translocation and transcriptional activity. Thus, STAT3 inhibition is useful to reduce vascular permeability in the setting of anaphylaxis.

Provided in certain embodiments herein are methods of treating, preventing, or reducing the risk or severity of an allergic reaction in an individual in need thereof, the method comprising administering to the individual a compound or composition described herein. In some embodiments, the allergic reaction is induced following an exposure to an allergen. In some embodiments, the allergen is a food allergen (such as milk, legumes, shellfish, tree nuts, eggs, fish, soy, and wheat), an environmental allergen or seasonal allergen (such as pollen or mold), a venom allergen (such as from wasp, bee, ant, hornet, yellow jacket, or asp), a medication allergen (such as anesthetics, β-lactam antibiotics, aspirin, non-steroidal anti-inflammatory drug, chemotherapy, vaccine, protamine, or herbal preparations), or latex. In some embodiments, the allergic reaction is anaphylaxis, anaphylactic shock, allergic rhinitis, urticaria, food allergy, drug allergy, hymenoptera allerga, bronchial constriction, asthma, or eczema.

STAT3 also plays an important role in viral infection and pathogenesis. Provided in certain embodiments herein are methods of treating, preventing, or reducing the risk or severity of a viral infection in an individual in need thereof, the method comprising administering to the individual a compound or composition described herein. In some embodiments, the viral infection is a chronic viral infection. In some embodiments, the chronic viral infection is AIDS, HIV infection, Hepatitis B infection, Hepatitis C virus infection, or Epstein-Barr virus infection.

In addition, reactive astrocytes in neurodegenerative diseases including Alzheimer's disease are implicated in STAT3 phosphorylation. Pathophysiological roles of astrocytes in the reactive state are thought to have important significance in the pathogenesis of neurodegenerative diseases. Provided in certain embodiments herein are methods of treating, preventing, or reducing the risk or severity of a neurodegenerative disease in an individual in need thereof, the method comprising administering to the individual a compound or composition described herein. In some embodiments, the neurodegenerative disease is chemotherapy-induced peripheral neuropathy, diabetic neuropathy, or chemobrain. Provided in certain embodiments herein are methods of treating, preventing, or reducing the risk or severity of pain in an individual in need thereof, the method comprising administering to the individual a compound or composition described herein. In some embodiments, pain is neuropathic pain. Provided in certain embodiments herein are methods of treating, preventing, or reducing the risk or severity of graft-versus-host diseases, pulmonary lymphangioleiomyomatosis, chagasic cardiomyopathy, age-related macular degeneration, amyloidosis, astrogliosis in Alzheimer's or other neurodegenerative diseases, or familial amyloid polyneuropathy.

STAT3 is involved in cytokine- and nutrient-induced insulin resistance, and excessive STAT3 signaling is implicated in the development of insulin resistance such as skeletal muscle insulin resistance in type 2 diabetes. Provided in certain embodiments herein are methods of treating, preventing, or reducing the risk or severity of insulin resistance in an individual in need thereof, the method comprising administering to the individual a compound or composition described herein. In some embodiments, the insulin resistance is a result of an underlying condition. In some embodiments, the insulin resistance is associated with muscle of the individual being treated. In some embodiments, the insulin resistance is caused by any reason for the individual, such as elevated free fatty acids in the blood, obesity, being overweight, having visceral fat, having a high fructose intake, having inflammation, being inactive, dysbiosis of the gut microbiota, and/or being genetically predisposed. In certain embodiments, any method provided herein is a method of treating, preventing, or reducing the risk or severity of medical conditions associated with insulin resistance or that are complications of insulin resistance at least in part, such as severe high blood sugar; severe low blood sugar; heart attack; stroke; kidney disease (including chronic, for example, chronic kidney disease (CKD)); eye problems; cancer; non-alcoholic fatty liver disease (NAFLD); polycystic ovarian syndrome (PCOS); metabolic syndrome; diabetes; or Alzheimer's disease, for example. In certain embodiments, the insulin resistance is a hallmark of metabolic syndrome and type 2 diabetes. Metabolic syndrome is a group of risk factors associated with type 2 diabetes and heart disease. Its symptoms include high blood triglycerides, blood pressure, belly fat, and blood sugar, as well as low HDL (good) cholesterol levels.

In some embodiments, the methods comprise administering a therapeutically effective amount of a composition disclosed herein to the individual. In certain embodiments, the method comprises administering at least 1 mg/kg/day of the compound of formula (I) to the individual. In certain embodiments, the method comprises administering at least 10 mg/kg/day of the compound of formula (I) to the individual. In certain embodiments, the method comprises administering at least 20 mg/kg/day of the compound of formula (I) to the individual. In certain embodiments, the method comprises administering at least 25 mg/kg/day of the compound of formula (I) to the individual.

EXAMPLES

Abbreviations:

As used herein the symbols and conventions used in these processes, schemes and examples are consistent with those used in the contemporary scientific literature, for example, the Journal of the American Chemical Society or the Journal of Biological Chemistry. Specifically, the following abbreviations may be used in the examples:

| | |
|---|---|
| g (grams); | mg (milligrams); |
| L (liters); | mL (milliliters); |
| μL (microliters); | psi (pounds per square inch); |
| M (molar); | mM (millimolar); |
| μmol (micromolar) | μm (micron) |
| MHz (megahertz); | mm (millimeter) |
| mol (moles); | mmol (millimoles); |
| rt (room temperature); | hr (hours); |
| min (minutes); | THF (tetrahydrofuran); |
| $CDCl_3$ (deuterated chloroform); | DMSO-$d_6$ (deuterated dimethylsulfoxide); |
| atm (atmosphere); | PE (petroleum ether) |
| EtOAc (ethyl acetate); | DCM (dichloromethane); |
| EtOH (ethanol); | t-Bu (tert-butyl); |
| MeOH (methanol); | ACN (acetonitrile); |
| $Na_2SO_4$ (sodium sulfate); | Boc (tert-butoxycarbonyl); |
| MTBE (methyl tert-butyl ether); | TFA (trifluoroacetic acid); |
| HCl (hydrochloric acid); | $Et_3N$ (triethylamine); |
| DPPA (diphenylphosphoryl azide); | $POCl_3$ (phosphorous oxychloride); |
| NaOH (sodium hydroxide); | FA (formic acid) |

Unless otherwise indicated, all temperatures are expressed in ° C. (degrees Centigrade). All reactions were conducted at room temperature unless otherwise noted. $^1$H-NMR spectra were recorded on a Bruker 400, or a Varian Unity-400 at 400 MHz field strength. Chemical shifts are expressed in parts per million (ppm, 8 units). Splitting patterns describe apparent multiplicities and are designated as s (singlet), d (doublet), t (triplet), q (quartet), m (multiplet), quin (quintet) or br (broad). The mass spec was run on a Sciex API 100 using electrospray ionization (ESI). The LC/MS was run using a C-18 reverse phase column (2.1 ID, 3.5 micron, 50 mm). Analytical thin layer chromatography was used to verify the purity as well as to follow the progress of reaction(s). Unless otherwise indicated, all final products were at least 95% pure as judged by HPLC/MS.

Example 1. Synthesis of Compounds

Exemplary compounds of Formula I were prepared according to the following methods.

1'-hydroxy-4'-((4-methoxyphenyl)sulfonamido)-[1,2'-binaphthalen]-2-ylmethyl(2-(methylamino)ethyl) carbamate hydrochloride (Compound 3)

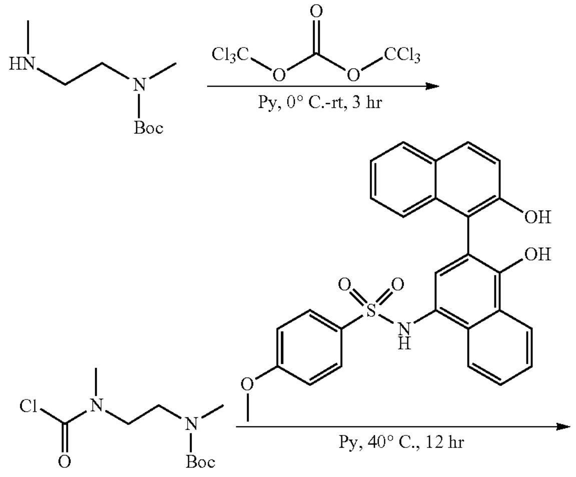

-continued

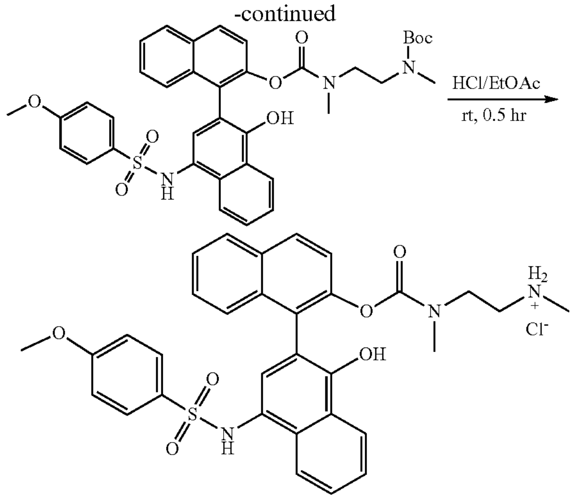

Compound 3

Step 1. Tert-butyl (2-((chlorocarbonyl)(methyl) amino)ethyl)(methyl)carbamate To a solution of tert-butyl N-methyl-N-[2-(methylamino) ethyl]carbamate (5.0 g, 26.56 mmol, 1.0 eq) in pyridine (50 mL) at 0° C. was added bis(trichloromethyl) carbonate (3.15 g, 10.62 mmol, 0.4 eq). The resulting reaction mixture was allowed to warm to rt and stirred for 3 hr. The reaction mixture was then concentrated under reduced pressure to afford the title compound as a solid, which was used immediately in the next step.

Step 2. tert-butyl (1'-hydroxy-4'-((4-methoxyphenyl) sulfonamido)-[1,2'-binaphthalen]-2-yl) ethane-1,2-diylbis(methylcarbamate)

To a solution of tert-butyl (2-((chlorocarbonyl)(methyl) amino)ethyl)(methyl)carbamate (6 g, 23.93 mmol, 1 eq) in pyridine (60 mL) at rt was added N-(1',2-dihydroxy-[1,2'-binaphthalen]-4'-yl)-4-methoxybenzenesulfonamide (TTI-101)(3.39 g, 7.18 mmol, 0.3 eq). The resulting solution was then heated to 40° C. and stirred for 12 hr. The reaction mixture was then concentrated under reduced pressure. The residue was then dissolved in EtOAc (200 mL), washed with 1.0 M HCl (1×200 mL), brine (1×100 mL), dried over $Na_2SO_4$, filtered, and concentrated under reduced pressure. The residue was purified by silica gel column chromatography (PE:EtOAc=10:1 to 1:1) to afford the title compound (3.5 g, 20% yield) as a solid. LCMS calculated for $C_{37}H_{39}N_3O_8S$: m/z=686. found: m/z=709 (M+Na).

Step 3: 1'-hydroxy-4'-((4-methoxyphenyl)sulfonamido)-[1,2'-binaphthalen]-2-yl methyl(2-(methylamino)ethyl)carbamate hydrochloride Tert-butyl (1'-hydroxy-4'-((4-methoxyphenyl)sulfonamido)-[1,2'-binaphthalen]-2-yl) ethane-1,2-diylbis(methylcarbamate)(3.5 g, 5.10 mmol, 1 eq) was dissolved in 4 N HCl/EtOAc (40 mL) and the resulting reaction mixture was stirred at rt for 0.5 hr. The reaction mixture was then diluted with MTBE (100 mL). The reaction mixture was then filtered. The collected solid was slurried with acetone (15 mL), warmed to 50° C., and stirred for 30 min, during which time the solids dissolved to form a clear solution. The solution was then cooled to 0° C. and stirred for 2 hr, during which time a precipitate formed. The resulting suspension was filtered to collect the solid. The solid was then dried under high vacuum to afford the title compound (1.56 g, 47% yield) as a solid. 1H NMR (400 MHZ, Methanol-$d_4$) δ=8.32 (m, 1H), 8.14 (m, 3H), 7.66 (m, 2H), 7.44 (m, 5H), 7.29 (m, 1H), 6.84 (m, 3H), 3.38 (s, 3H), 3.42-3.32 (m, 2H), 2.84 (m, 2H), 2.73 (m, 2H), 2.57 (m, 2H), 2.13 (s, 3H). LCMS calculated for $C_{32}H_{31}N_3O_6S$: m/z=585. found: m/z=586 (M+H).

2-hydroxy-4'-((4-methoxyphenyl)sulfonamido)-[1,2'-binaphthalen]-1'-yl methyl(3-(methylamino)propyl) carbamate hydrochloride (Compound 4)

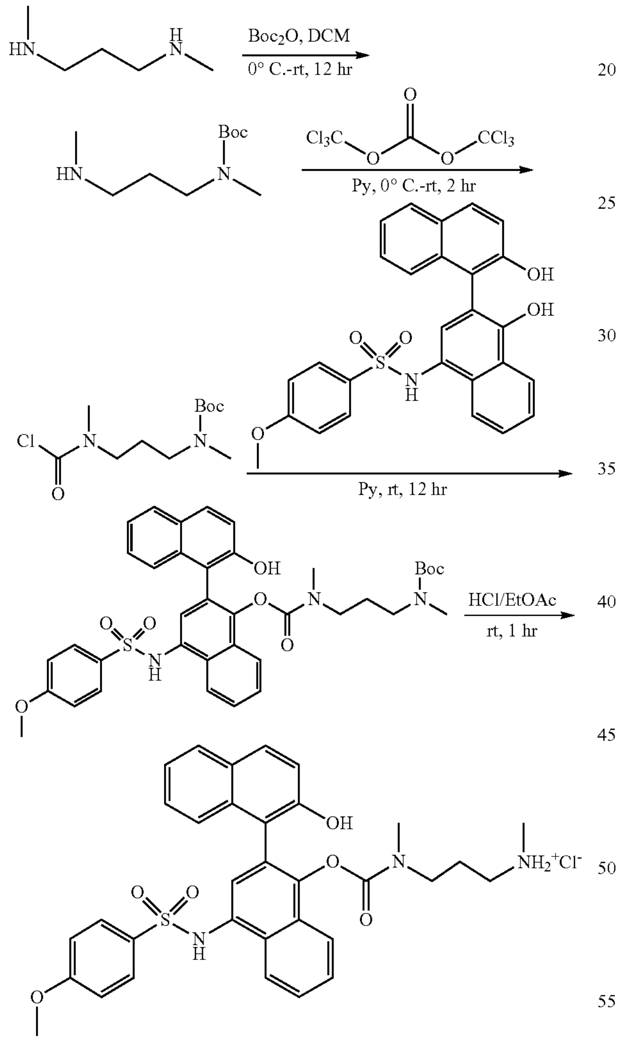

Compound 4

Step 1: Tert-butyl N-methyl-N-(3-(methylamino)propyl)carbamate

To a solution of N,N'-dimethylpropane-1,3-diamine (5.0 g, 48.93 mmol, 1.0 eq) in DCM (100 mL) at 0° C. was added tert-butoxycarbonyl tert-butyl carbonate (4.27 g, 19.57 mmol, 4.50 mL, 0.4 eq) in DCM (80 mL). The resulting reaction mixture was allowed to warm to rt and stirred for 12 hr. The reaction mixture was then concentrated under reduced pressure and the residue was dissolved in $H_2O$ (300 mL) and extracted with PE (2×150 mL). The aqueous phase was then extracted with DCM (5×200 mL). The combined DCM layers were washed with brine (1×300 mL), dried over $Na_2SO_4$, filtered, and concentrated under reduced pressure to afford the title compound (8.1 g, 27% yield) as an oil. 1H NMR: (400 MHz, $CDCl_3$) δ=3.21 (m, 2H), 2.77 (s, 3H), 2.49 (t, J=6.8, 2H), 2.37 (m, 4H), 1.60 (m, 2H), 1.39 (s, 9H).

Step 2: Tert-butyl (2-((chlorocarbonyl)(methyl)amino)propyl)(methyl)carbamate

To a solution of tert-butyl N-methyl-N-(3-(methylamino)propyl)carbamate (6.0 g, 29.66 mmol, 1.0 eq) in pyridine (60 mL) at 0° C. was added bis(trichloromethyl) carbonate (3.52 g, 11.86 mmol, 0.4 eq). The resulting reaction mixture was allowed to warm to rt and stirred for 2 h. The reaction mixture was then concentrated under reduced pressure to afford the title compound as a solid, which was used immediately in the next step.

Step 3: Tert-butyl (2-hydroxy-4'-((4-methoxyphenyl)sulfonamido)-[1,2'-binaphthalen]-1'-yl) propane-1,2-diylbis(methylcarbamate)

To a solution of N-(1',2-dihydroxy-[1,2'-binaphthalen]-4'-yl)-4-methoxybenzenesulfonamide (TTI-101)(4.27 g, 9.07 mmol, 0.3 eq) in pyridine (100 mL) at rt was added tert-butyl (2-((chlorocarbonyl)(methyl)amino)propyl)(methyl)carbamate (8 g, 30.22 mmol, 1.0 eq). The resulting reaction mixture was then heated to 40° C. and stirred for 12 h. The reaction mixture was cooled to rt and concentrated under reduced pressure. The residue was dissolved in $H_2O$ (200 mL) and the mixture was adjusted to pH of 2 by addition of 1 M HCl. The aqueous solution was then extracted with EtOAc (3×150 mL). The combined organic layers were washed with brine (1×250 mL), dried over $Na_2SO_4$, filtered, and concentrated under reduced pressure to give a residue. The residue was purified by silica gel column chromatography (PE:EtOAc=5:1 to 1:1) to afford the title compound (4.4 g, 18% yield) as a solid. LCMS calculated for $C_{38}H_{41}N_3O_8S$: m/z=700. found: m/z=723 (M+Na).

Step 4: 2-hydroxy-4'-((4-methoxyphenyl)sulfonamido)-[1,2'-binaphthalen]-1'-yl methyl(3-(methylamino)propyl)carbamate hydrochloride To a solution of tert-butyl (2-hydroxy-4'-((4-methoxyphenyl)sulfonamido)-[1,2'-binaphthalen]-1'-yl) propane-1,2-diylbis(methylcarbamate)(4.4 g, 6.29 mmol, 1.0 eq) in EtOAc (40 mL) at rt was added 4 N HCl/EtOAc (20 mL). The resulting reaction mixture was stirred at rt for 1 hr. The reaction mixture was then concentrated under reduced pressure to give a residue. The residue was purified by preparative reverse-phase HPLC (Phenomenex Luna C18 column (250×70 mm×15 μm); mobile phase: [water (0.04% HCl)-ACN]; B %: 14%-44%, 20 min) to give 3 g of material. The material was added into acetone (30 mL) and heated to 50° C. with stirring for 30 min, during which time the solid dissolved to form a clear solution. The solution was then cooled to 0° C. and stirred for 2 hr, during which time a precipitate formed. The resulting suspension was filtered to collect the solid. The solid was then dried under high vacuum to afford the title compound (1.4 g, 36% yield) as a solid. 1H NMR: (400 MHz, Methanol-$d_4$) δ=8.28 (m, 1H), 8.14 (m, 1H), 8.00 (m, 2H), 7.68-7.48 (m, 5H), 7.43-7.21 (m, 3H), 6.85 (m, 3H), 3.70 (s, 3H), 3.29-3.13 (m, 2H), 2.84 (m, 1H), 2.70 (s, 3H), 2.58 (m, 2H), 2.47 (m, 1H), 2.28 (m, 1H), 1.68-1.52 (m, 2H). The regioisomeric location of the carbamate is not unambiguously confirmed by NMR spectroscopy. LCMS calculated for $C_{33}H_{33}N_3O_6S$: m/z=599. found: m/z=600 (M+).

(2S)-2-amino-4-((((2-hydroxy-4'-((4-methoxyphenyl)sulfonamido)-[1,2'-binaphthalen]-1'-yl)oxy)carbonyl)amino)butanoic acid hydrochloride (Compounds 6A, 6B, 6C)

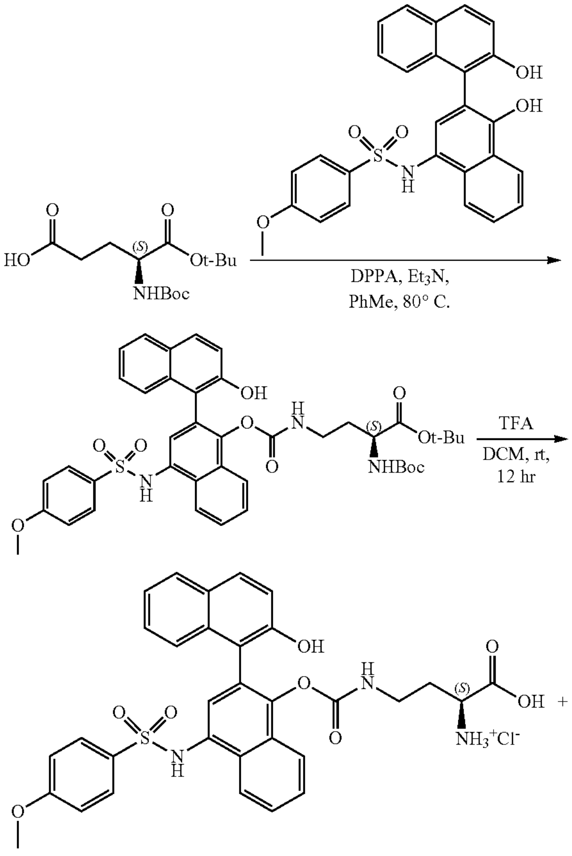

Compound 6A*

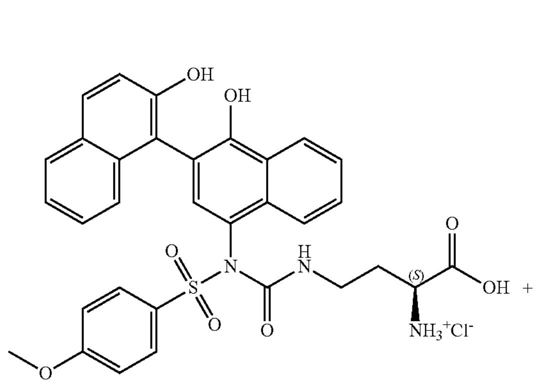

Compound 6B*

-continued

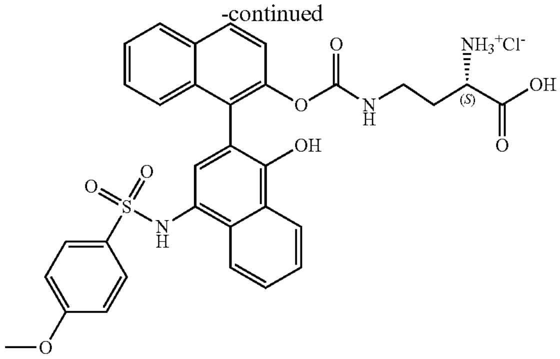

Compound 6C*

Step 1: Tert-butyl (2S)-2-((tert-butoxycarbonyl)amino)-4-((((2-hydroxy-4'-((4-methoxyphenyl)sulfonamido)-[1,2'-binaphthalen]-1'-yl)oxy)carbonyl)amino)butanoate To a solution of (4S)-5-tert-butoxy-4-(tert-butoxycarbonylamino)-5-oxo-pentanoic acid (1.0 g, 3.30 mmol, 1.0 eq) in toluene (10 mL) at rt was added DPPA (1.36 g, 4.94 mmol, 1.07 mL, 1.5 eq) and $Et_3N$ (667 mg, 6.59 mmol, 917.67 μL, 2.0 eq). The resulting reaction mixture heated to 80° C. and stirred for 1 hr, then was cooled to rt. Next, N-(1',2-dihydroxy-[1,2'-binaphthalen]-4'-yl)-4-methoxybenzenesulfonamide (TTI-101)(1.09 g, 2.31 mmol, 0.7 eq) was added, and the resulting reaction mixture was stirred at rt for 12 hr. The mixture was concentrated under reduced pressure. The residue was purified by silica gel column chromatography (PE:EtOAc=0:1 to 1:1) to give the product. The product was purified by reverse-phase column chromatography (ACN:$H_2O$=0:1-1:1) to afford the title compound (4.8 g, 33% yield) as a solid and mixture of three regioisomers and used in the next step. LCMS calculated for $C_{41}H_{45}N_3O_{10}S$: m/z=771. found: m/z=794 (M+Na).

Step 2: (2S)-2-amino-4-((((2-hydroxy-4'-((4-methoxyphenyl)sulfonamido)-[1,2'-binaphthalen]-1'-yl)oxy)carbonyl)amino)butanoic acid hydrochloride To a solution of tert-butyl (2S)-2-((tert-butoxycarbonyl)amino)-4-((((2-hydroxy-4'-((4-methoxyphenyl)sulfonamido)-[1,2'-binaphthalen]-l'-yl)oxy)carbonyl)amino)butanoate (4.8 g, 6.22 mmol, 1.0 eq) in DCM (50 mL) at rt was added TFA (14.18 g, 124.37 mmol, 9.21 mL, 20 eq). The resulting mixture was stirred at rt for 12 hr. The mixture was concentrated under reduced pressure, and the residue was purified by preparative reverse-phase HPLC(Phenomenex Luna C18 column (250×70 mm×15 μm); mobile phase: [water (0.04% HCl)-ACN]; B %: 25%-30%, 20 min) to afford three isomers. The isomers were randomly assigned as Compound 6A, 6B, and 6C. Isomer 6A: 600 mg, solid. 1H NMR (400 MHz, DMSO-$d_6$) δ=10.03 (s, 1H), 9.49 (s, br, 1H), 8.29 (m, 1H), 8.18 (m, 2H), 7.78 (m, 3H), 7.70-7.55 (m, 5H), 7.21 (m, 3H), 6.98 (m, 3H), 6.77 (s, 1H), 3.63 (m, 4H), 2.90 (m, 2H), 1.76 (m, 1H), 1.62 (m, 2H); LCMS calculated for $C_{32}H_{29}N_3O_8S$: m/z=615. found: m/z=616 (M+H). Isomer 6B: 640 mg, solid. 1H NMR (400 MHZ, DMSO-$d_6$) δ=10.05 (s, 1H), 9.49 (s, br, 1H), 8.29 (m, 4H), 7.78 (m, 3H), 7.61 (m, 5H), 7.25 (m, 3H), 6.98 (m, 3H), 6.78 (s, 1H), 3.77 (m, 1H), 3.61 (s, 3H), 2.95 (m, 2H), 1.29 (m, 2H); LCMS calculated for $C_{32}H_{29}N_3O_8S$: m/z=615. found: m/z=616

(M+H). Isomer 6C: 850 mgs, solid. 1H NMR (400 MHZ, DMSO-$d_6$) δ=9.72 (s, 1H), 9.07 (s, 1H), 8.23 (m, 4H), 7.98 (m, 3H), 7.57-7.41 (m, 9H), 7.19 (m, 1H), 6.98 (2, J=8.8, 2H), 6.75 (s, 1H), 3.89 (m, 1H), 3.69 (s, 3H), 3.18 (m, 2H), 1.90 (m, 2H). LCMS calculated for $C_{32}H_{29}N_3O_8S$: m/z=615. found: m/z=616 (M+H).

N-((6)-6-hydroxy-6-oxidodinaphtho[1,2-d: 1',2'-f][1,3,2]dioxaphosphepin-15-yl)-4-methoxybenzenesulfonamide (Compound 9A) and 2-hydroxy-4'-((4-methoxyphenyl)sulfonamido)-[1,2'-binaphthalen]-1'-yl dihydrogen phosphate (Compound 9)

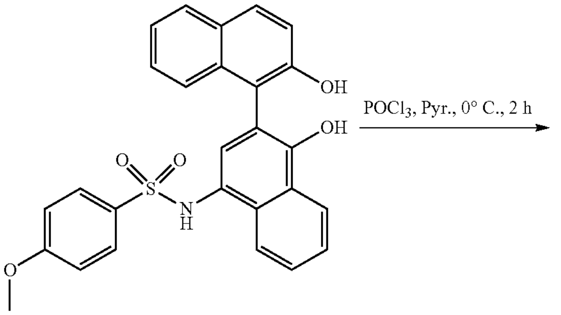

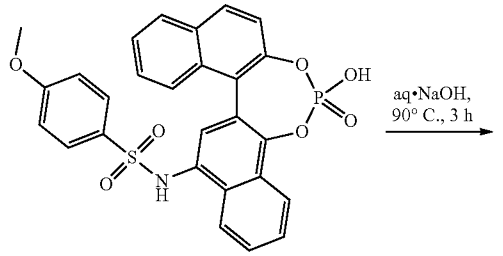

Compound 9A

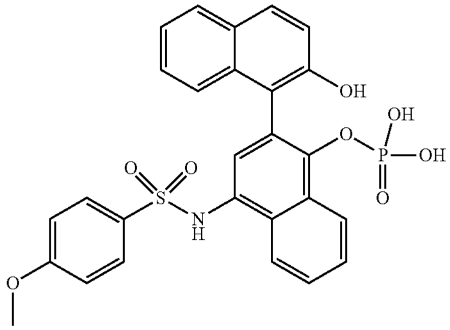

Compound 9

Step 1: N-((6)-6-hydroxy-6-oxidodinaphtho[1,2-d: 1',2'-f][1,3,2]dioxaphosphepin-15-yl)-4-methoxybenzenesulfonamide To a solution of N-(1',2-dihydroxy-[1,2'-binaphthalen]-4'-yl)-4-methoxybenzenesulfonamide (TTI-101)(3.0 g, 6.36 mmol, 1.0 eq) in pyridine (30 mL) at 0° C. was added $POCl_3$ (975 mg, 6.36 mmol, 591 μL, 1.0 eq). The resulting reaction mixture was stirred at 0° C. for 2 hr. The reaction was poured into ice water, and the pH was adjusted to pH=8 with 1N NaOH. The solution was concentrated under reduced pressure to give a residue. The residue was purified by preparative reverse-phase HPLC(Phenomenex Gemini-NX C18 75×30 mm×3 μm column; mobile phase: [$H_2O$ (10 mM $NH_4HCO_3$)-ACN]; B %: 20%-50%, 8 min) to afford the product as a solid. The solid was added into EtOH/acetone (324 mL, 1:5). The resulting slurry was heated to 50° C. for 30 min, during which time the solid dissolved to afford a clear solution. The solution was then cooled to 0° C. and stirred for 2 hr, during which time a precipitate formed. The resulting suspension was filtered to collect the solid. The solid was then dried under high vacuum to afford the title compound (578 mg, 19% yield) as a solid. $^1H$ NMR: (400 MHZ, Methanol-$d_4$) δ=10.16 (s, br, 1H), 8.27 (d, 1H), 8.19 (d, 1H), 8.01 (dd, 2H), 7.74 (d, 2H), 7.59 (m, 3H), 7.50 (m, 1H), 7.34-7.24 (m, 4H), 7.16 (s, br, 1H), 7.08 (d, 2H), 3.81 (s, 3H); LCMS calculated for $C_{27}H_{20}NO_7PS$: m/z=533. found: m/z=532 (M−H).

Step 2:2-hydroxy-4'-((4-methoxyphenyl)sulfonamido)-[1,2'-binaphthalen]-1'-yl dihydrogen phosphate A solution of N-((6)-6-hydroxy-6-oxidodinaphtho[1,2-d: 1',2'-f][1,3,2]dioxaphosphepin-15-yl)-4-methoxybenzenesulfonamide (2 g, 3.75 mmol, 1.0 eq) in NaOH (1 M, 11.25 mL, 3.0 eq) was heated to 80° C. with stirring for 3 hr. The reaction mixture was then concentrated under reduced pressure. The residue was purified by preparative reverse-phase HPLC(Welch Xtimate C18 250×70 mm×10 μm column; mobile phase: [H2O (10 mM $NH_4HCO_3$)-ACN]; B %: 3%-30%, 25 min) to afford 650 mg of the product. The product was added into EtOH/i-PrOH (5 mL, 1:3). The resulting slurry was stirred and heated to 50° C. for 30 min, during which time the solid dissolved completely to form a clear solution. The solution was then cooled to 0° C. and stirred for 2 hr, during which time a precipitate formed. The resulting suspension was filtered to collect the solid. The solid was then dried under high vacuum to afford the title compound (160 mg, 22% yield) as a solid. 1H NMR: (400 MHz, Methanol-$d_4$) δ=8.62 (d, 1H), 8.19 (d, 1H), 7.79 (d, 1H), 7.74 (d, 1H), 7.49 (m, 4H), 7.24 (m, 2H), 7.11 (d, 1H), 6.77 (d, 2H), 6.59 (d, 1H), 6.40 (s, 1H), 3.62 (m, 3H). LCMS calculated for $C_{27}H_{22}NO_8PS$: m/z=551, found: m/z=552 (M+H).

2-hydroxy-4'-((4-methoxyphenyl)sulfonamido)-[1,2'-binaphthalen]-1'-yl(((R)-pyrrolidin-2-yl)methyl) carbamate (Compounds 15A and 15B)

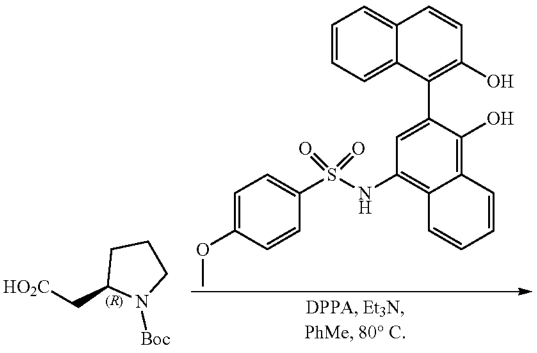

-continued

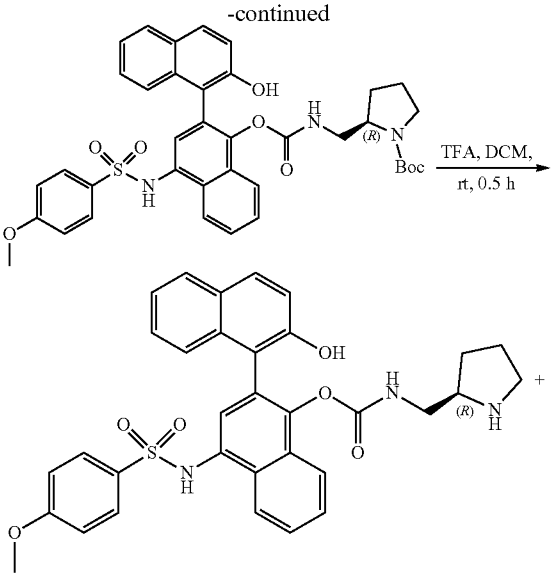

Compound 15A

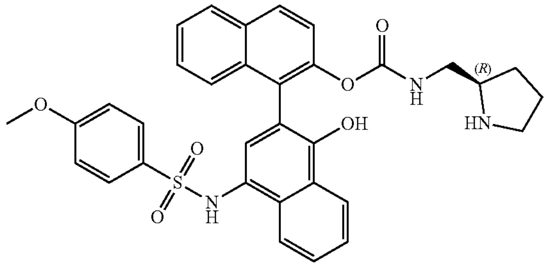

Compound 15B

Step 1: Tert-butyl (2R)-2-(((((2-hydroxy-4'-((4-methoxyphenyl)sulfonamido)-[1,2'-binaphthalen]-1'-yl)oxy)carbonyl)amino) methyl) pyrrolidine-1-carboxylate To a solution of (R)-2-(1-(tert-butoxycarbonyl) pyrrolidin-2-yl) acetic acid (3.8 g, 16.57 mmol, 1.0 eq) in toluene (40 mL) at rt was added $Et_3N$ (3.35 g, 33.15 mmol, 4.61 mL, 2.0 eq) and DPPA (6.84 g, 24.86 mmol, 5.39 mL, 1.5 eq). The resulting reaction mixture was heated at 80° C. and stirred for 1 hr. The reaction mixture was cooled to rt, and then added into a solution of N-(1',2-dihydroxy-[1,2'-binaphthalen]-4'-yl)-4-methoxybenzenesulfonamide (TTI-101)(7.82 g, 16.57 mmol, 1.0 eq) in toluene (40 mL). The resulting reaction mixture was stirred at rt for 2 hr. The reaction mixture was poured into $H_2O$ (200 mL) extracted with EtOAc (2×100 mL). The combined organic layers were washed with brine (50 mL), dried over $Na_2SO_4$, filtered, and concentrated under reduced pressure to give a residue. The residue was purified by reverse-phase HPLC((Phenomenex Luna C18 column (250×70 mm×15 μm); mobile phase: [water (0.04% HCl)-ACN]; B %: 20%-80%, 20 min)) to afford the title compound (4.8 g, 42% yield) as a solid and mixture of two regioisomers. LCMS calculated for $C_{38}H_{39}N_3O_8S$: m/z=697. found: m/z=720 (M+Na).

Step 2:2-hydroxy-4'-((4-methoxyphenyl)sulfonamido)-[1,2'-binaphthalen]-1'-yl(((R)-pyrrolidin-2-yl) methyl)carbamate hydrochloride To a solution of tert-butyl (2R)-2-(((((2-hydroxy-4'-((4-methoxyphenyl)sulfonamido)-[1,2'-binaphthalen]-1'-yl) oxy)carbonyl)amino) methyl) pyrrolidine-1-carboxylate (4.8 g, 6.88 mmol, 1.0 eq) in DCM (50 mL) at rt was added TFA (15.69 g, 137.58 mmol, 10.19 mL, 20 eq). The resulting reaction mixture was stirred at rt for 30 min. The mixture was concentrated under reduced pressure. The residue was purified by preparative reverse-phase HPLC(Phenomenex Luna C18 (250×70 mm×15 μm column); mobile phase: [H2O (0.04% HCl)-ACN]; B %: 16%-46%, 20 min) to afford the title compound as two isomers, which were randomly assigned as Compound 15A and 15B. Isomer 15A was subsequently triturated with Acetone:ACN (30 mL, 1:1) and the resulting solid was isolated by filtration and dried under high vacuum to provide 1.2 g of material as a solid. 1H NMR (400 MHZ, Methanol-$d_4$) δ=8.24 (m, 1H), 7.98 (m, 3H), 7.58 (m, 2H), 7.54-7.41 (m, 5H), 7.30 (m, 1H), 6.92 (m, 3H), 3.69 (s, 3H), 3.46-3.09 (m, 3H), 3.02 (m, 2H), 1.67 (m, 3H), 1.27 (m, 1H); LCMS calculated for $C_{33}H_{31}N_3O_6S$: m/z=597. found: m/z=598 (M+H). Isomer 15B was subsequently added into Acetone:EtOAc (20 mL, 1:1). The resulting slurry was stirred and heated to 50° C. for 30 min, during which time the solid dissolved completely and a solution formed. The solution was then cooled to 0° C. and stirred for 2 hr, during which time a precipitate formed. The resulting suspension was filtered to collect the solid. The solid was then dried under high vacuum to provide 400 mg of material as a solid. 1H NMR (400 MHZ, DMSO-$d_6$) δ=10.03 (s, br, 1H), 9.49 (m, 1H), 9.06-8.67 (s, br, 1H), 8.23 (m, 2H), 7.86-7.59 (m, 8H), 7.22 (m, 3H), 6.93 (m, 3H), 6.77 (m, 1H), 3.71 (s, 3H), 3.27-3.07 (m, 2H), 3.04-2.86 (m, 2H), 1.69-1.22 (m, 3H), 1.10-0.83 (m, 1H); LCMS calculated for $C_{33}H_{31}N_3O_6S$: m/z=597. found: m/z=598 (M+H).

Synthesis of following compounds were attempted, but could not be isolated due to the lability of the compounds:

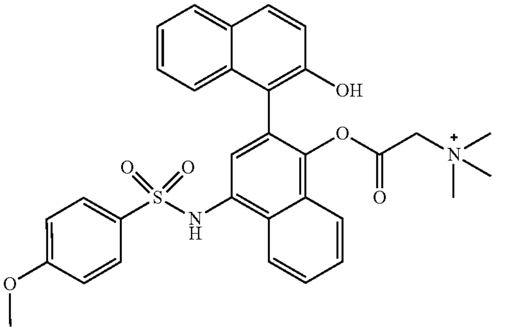

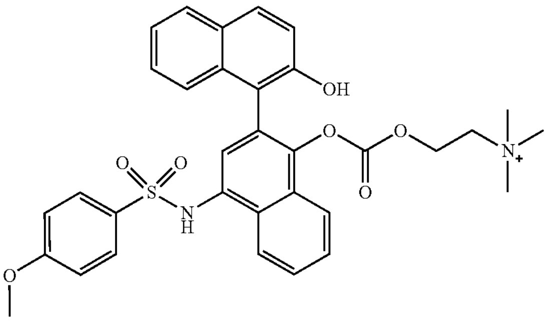

-continued

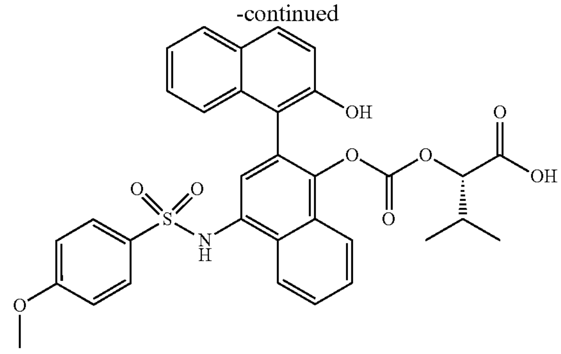

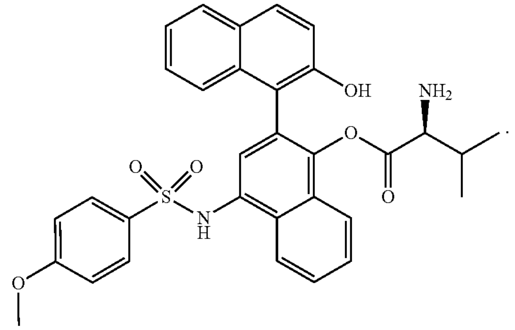

Example 2. Solubility, Human Plasma Stability, and Aqueous Stability of the Compounds Solubility, plasma stability, and aqueous stability were evaluated for the compounds (Table 1).

TABLE 1

Solubility, plasma stability, and aqueous stability of compounds of Formula I.

| Compound No. | Solubility (pH = 2.0) ug/mL | Solubility (pH = 7.4) ug/mL | Human Plasma Stability | Aqueous Stability (pH = 7.4) | Aqueous Stability (pH = 3.5) | Aqueous Stability (pH = 2.0) |
|---|---|---|---|---|---|---|
| 3 | 1250 | <1.0 | t½ = 9.1, 11.8 min | Unstable; t½ < 20 min (n = 2) | Stable (n = 2) | Stable (n = 2) |
| 4 | 1391 | <1.0 | t½ = 4.3 min | Unstable; t½ = 60 min | Stable | Stable |
| 6A | 684 | 22 | t½ = 11.8 min | Unstable; t½ = 80 min | Stable | Stable |
| 6B | 130 | 7 | t½ = 12.9 min | Unstable; t½ = 40 min | Stable | Stable |
| 6C | 167 | <1 | t½ = 12.2 min | Unstable; t½ = 40 min | Stable | Stable |
| 9 | 1534 | 6161, 4501 | Stable | Stable (n = 2) | Stable (n = 2) | Stable |
| 9A | 56 | 37, 12 | Stable | Stable (n = 2) | Stable (n = 2) | Stable |
| 15A | 5379 | <1 | t½ = 5.4 min | Unstable; t½ < 5 min | Stable | Stable |
| 15B | 121 | <1 | t½ = 11.6 min | Unstable; t½ < 5 min | Stable | Stable |

Aqueous Stability

For Compound 3, Compound 4, Compound 6A, Compound 6B, Compound 6C, Compound 15A, Compound 15B:

For each compound, 10 μL of 10 mM DMSO stock solution was added to 490 μL DMSO to yield 200 μM working solution. Then 2 μL of 200 μM working solution was added to 96-deep-well plates corresponding to T0, T60, T120, T360, and T1440. Then 198 μL of 75 mM Phosphate Buffer (pH 2.0, 3.5, 7.4) solutions were added to above corresponding well except T0 to reach 2 μM as final test concentration for each time point (60, 120, 360, 1440 minutes). The final concentration of DMSO in the incubation mixture was 1%. The samples were incubated at 37° C., 600 rpm for the appointed time. Test samples at corresponding time point (60, 120, 360, 1440 minutes) were removed at the end of incubation time and immediately mixed with 400 μL of cold acetonitrile containing 200 ng/mL tolbutamide & labetalol (internal standard) and 0.3% FA. Then 200 μL of the resulting suspension was further diluted with 400 μL of cold acetonitrile containing 200 ng/mL tolbutamide & labetalol and 0.3% FA. The TO samples were prepared by transferring 198 μL of 75 mM Phosphate Buffer (pH 2.0, 3.5, 7.4) to corresponding well after adding 400 μL of cold acetonitrile containing 200 ng/mL tolbutamide and labetalol and 0.3% FA. Then 200 μL of the resulting suspension was further diluted with 400 μL of cold acetonitrile containing 200 ng/ml tolbutamide and labetalol and 0.3% FA. Samples were subjected to centrifuge at 4000 rpm, 4° C. for 20 min and 60 μL of supernatant was pipetted and mixed with 180 μL of purified water, mixed for LC/MS/MS analysis. The % remaining of test compound at each incubation time was calculated based on peak area ratio of analyte/IS:

$$\%\ \text{Remaining (at Appointed Time)} = \frac{PAR_T}{PAR_0} \times 100$$

where $PAR_T$: peak area ratio at appointed time; $PAR_0$: peak area ratio of T0 incubation; and PAR: peak area ratio, the ratio of peak area of analyte and internal standard For Compound 9, Compound 9A:

For each compound, 10 μL of 10 mM DMSO stock solution was added to 490 μL DMSO to yield 200 μM working solution. Then 2 μL of 200 μM working solution was added to 96-deep-well plates corresponding to T0, T60, T120, T360, and T1440. Then 198 μL of 75 mM Phosphate Buffer (pH 2.0, 3.5, 7.4) solutions were added to above corresponding well except T0 to reach 2 μM as final test concentration for each time point (60, 120, 360, 1440 minutes). The final concentration of DMSO in the incubation mixture was 1%. The samples were incubated at 37° C., 600 rpm for the appointed time. Test samples at corresponding time point (60, 120, 360, 1440 minutes) were removed at the end of incubation time and immediately mixed with 400 μL of cold acetonitrile containing 200 ng/ml tolbutamide & labetalol (internal standard). Then 200 μL of the resulting suspension was further diluted with 400 μL of cold acetonitrile containing 200 ng/mL tolbutamide & labetalol. The TO samples were prepared by transferring 198 μL of 75 mM Phosphate Buffer (pH 2.0, 3.5, 7.4) to corresponding well after adding 400 μL of cold acetonitrile containing 200 ng/mL tolbutamide and labetalol. Then 200 μL of the resulting suspension was further diluted with 400 μL of cold acetonitrile containing 200 ng/mL tolbutamide and labetalol. Samples were subjected to centrifuge at 4000 rpm, 4° C. for 20 min, and 60 μL of supernatant was pipetted and mixed with 180 μL of purified water for LC/MS/MS analysis. The % remaining of test compound at each incubation time was calculated based on peak area ratio of analyte/IS.

Solubility

For each compound, 450 μL of 75 mM phosphate buffer (pH 2.0 and 7.4) were added to get an over-saturated suspension. The mixture was vortexed for at least 2 minutes. The samples were shaken for 24 hours at rt at 800 rpm then centrifuged. The suspensions were filtered through a PTFE filter media. The filtrates were analyzed by HPLC(Column: Waters XBridge C18 4.6*100 M; Mobile Phase A: 0.1% TFA in Water; Mobile Phase B: 0.1% TFA in Acetonitrile) and concentration was calculated with a standard curve.

Plasma Stability

98 μL/well of blank plasma were added to all 96-well reaction plates (Blank, TO, T10, T30, T60, and T120). 2 L/well of working solution of each compound (100 μM) was added to all reaction plates except Blank. All reaction plates containing mixtures of compound and plasma were incubated at 37° C. in water bath. At the end of incubation, 400 μL of stop solution (200 ng/mL tolbutamide and 200 ng/mL labetalol in ACN, optionally 0.1% FA) was added to precipitate protein, shaken, and centrifuged. The supernatant was analyzed by LC-MS/MS.

Example 3. Pharmacokinetics of the Compounds in Mice, Rats, and Monkeys

Pharmacokinetics of TTI-101 and the compounds of Formula I were evaluated in rats, following single intravenous (IV) bolus of TTI-101 and oral (PO) gavage the compounds of Formula I.

Twenty-four male SD rats were divided into four groups with 6 animals/group in four studies. Animals in Group 1 were administered TTI-101 at 21.5 mg/kg by single IV bolus. Animals in Groups 2, 3 and 4 were administered Compound 3, Compound 4 and Compound 9 at doses equivalent to 17.8, 18.1, and 19.2 mg/kg TTI-101, respectively, by single PO administration. Plasma samples were collected at pre-dose (0), 0.083 (IV only), 0.5, 1, 2, 4, 8 and 24 hours post-dose. Concentrations of TTI-101 in plasma samples were determined by LC-MS/MS. The vehicle used for IV study was DMSO/EtOH/PEG400/Saline (5/2/43/50% v/v). The vehicle used for PO studies was 0.5% methylcellulose (400 cps) in 50 mM citrate buffer, pH~3.5 or PBS, pH~7.4.

In addition, TTI-101 that was orally administered as self-emulsifying drug dispersion (SEDD) as prepared according to methods as described in WO 2021/150912, demonstrated F %=40.4 in rats.

Table 2 shows exemplary PK data of compounds of Formula I in rats.

TABLE 2

| Compound No. | Dose Administered | Formulation | $AUC_{last}$[1] | $T_{max}$/ $T_{1/2}$ | F % |
|---|---|---|---|---|---|
| TTI-101 | 21.5 mg/kg | 5 mg/mL in DMSO/EtOH/ PEG400/Saline | 72431 ± 15138 ng*h/ mL[1] | ND/ 2.8 ± 0.6 h | |
| 3 | 22.1 mg/kg | 2.5 mg/mL in 0.5% MC in 50 mM citrate buffer | 23447 ± 9286 ng*h/mL[1] | 4.0 h/ 2.4 ± 0.5 h | 39.1 |
| 9 | 22.4 mg/kg | 2.5 mg/mL in PBS | 37775 ± 14217 ng*h/mL[2] | 1.8 ± 1.7 h/ 2.0 ± 0.4 h | 58.5 |
| 4 | 23.0 mg/kg | 2.5 mg/mL in 0.5% MC in 50 mM citrate buffer | 570 ± 247 ng*h/mL | 4 h/ ND | 0.9 |

[1]Measurable plasma concentration at 24 hours, thus $AUC_{last}$ is to 24 hours.

[2]Measurable plasma concentration at 8 hours, thus $AUC_{last}$ is to 8 hours. F % is likely to be underestimated.

MC = methylcellulose

PBS = phosphate-buffered saline

ND = not determined

F = bioavailability, calculated on dose levels

Pharmacokinetics of TTI-101 and the compounds of Formula I were evaluated in monkeys, following single intravenous (IV) bolus or oral (PO) gavage of TTI-101 and oral (PO) gavage the compounds of Formula I.

A group of 3 male cynomolgus monkeys were used in this 5-phase study. Animals in Phase 1 were administered TTI-101 by single intravenous bolus administration at 26 mg/kg. Animals in Phases 2, 3, 4 and 5 were administered TTI-101 SEDD, Compound 3, Compound 9A and Compound 9 by single oral administration, respectively. Plasma samples were collected at pre-dose (0), 0.083 (Phase 1 only), 0.5, 1, 2, 4, 8 and 24 hours (except Phase 1) post-dose for Phases 1, 2, 3, 4 and 5. Concentrations of TTI-101 in plasma samples were determined by LC-MS/MS. The SEDD formulation of TTI-101 was prepared according to methods as described in WO 2021/150912.

Table 3 shows exemplary PK data of compounds of Formula I in monkeys.

TABLE 3

| Compound | Dose Administered | Formulation | $AUC_{last}$ | $T_{max}/T_{1/2}$ | F % |
|---|---|---|---|---|---|
| TTI-101 | 26.0 mg/kg | 25 mg/mL in DMSO/EtOH/PEG400/PBS (5:5:70:20) | 116422 ± 7170 ng*h/mL[2] | ND/ 2.4 ± 0.1 h | |
| TTI-101 | 53.5 mg/kg | 15.5 mg/mL in SEDD | 123040 ± 15588 ng*h/mL[1] | 2.0 h/ 9.0 ± 3.7 h | 51.4 |
| 3 | 21.9 mg/kg (17.6 mg/kg TTI-101 equiv.) | 5 mg/mL in 0.5% MC at pH 3.5 in 50 mM citrate buffer | 32477 ± 11797 ng*h/mL[1] | 6.7 ± 2.3 h/ ND | 41.2 |
| 9 | 24.3 mg/kg (20.8 mg/kg TTI-101 equiv.) | 2.5 mg/mL in PBS, pH 2.7 homogenous suspension | 75704 ± 14050 ng*h/mL[2] | 1.7 ± 0.6 h/ 6.7 ± 1.4 h | 81.3 |
| 9A | 26.3 mg/kg (23.2 mg/kg TTI-101 equiv.) | 5 mg/mL 0.5% MC at pH 3.5 in 50 mM citrate buffer | 5203 + 1048 ng*h/mL[1] | 8.0 ± 0 h/ ND | 6.7 |

[1]Measurable plasma concentration at 24 hours, thus $AUC_{last}$ is to 24 hours.
[2]Measurable plasma concentration at 8 hours, thus $AUC_{last}$ is to 8 hours. F % is likely to be underestimated.
MC = methylcellulose
PBS = phosphate-buffered saline
ND = not determined
F = bioavailability, calculated on dose levels H22 (HCC model) syngeneic mice were treated with Compound 9 (for example, in PBS, at 34, 69, and 103 mg/kg, which are TTI-101 equivalence of 25, 50, and 75 mg/kg, respectively) and TTI-101 SEDD (for example, at 50 mg/kg) orally twice a day. The FIGURE shows the exposure profile comparing Compound 9 and TTI-101 SEDD. The FIGURE shows that Compound 9 has more than three times the exposure in mice than TTI-101 SEDD by Day 21.

The invention claimed is:

1. A compound of Formula I-B:

(I-B)

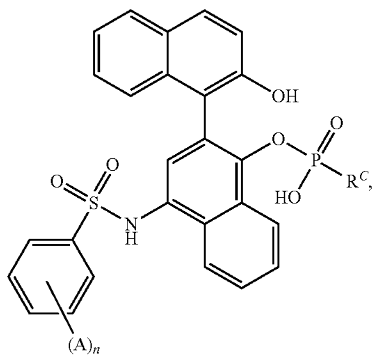

or a pharmaceutically acceptable salt or a solvate thereof, wherein

A is halo, $C_{1-4}$ alkyl, $C_{1-4}$ alkoxy, $C_{1-4}$ haloalkyl, or $C_{1-4}$ haloalkoxy;

$R^C$ is hydroxy; and n is 0 or 1.

2. The compound of claim 1, wherein A is $C_{1-4}$ alkoxy.

3. A pharmaceutical composition comprising: a) a compound of claim 1, or a pharmaceutically acceptable salt or a solvate thereof, and b) a pharmaceutically acceptable carrier.

4. A method of treating cancer by inhibiting signal transducer and activator of transcription 3 (STAT3) in an individual in need thereof, comprising administering to the individual an effective amount of a compound of claim 1, or a pharmaceutically acceptable salt or a solvate thereof.

5. The method of claim 4, wherein the cancer is head and neck cancer, lung cancer, liver cancer, breast cancer, skin cancer, kidney cancer, testicular cancer, colon cancer, rectal cancer, gastric cancer, metastatic melanoma, prostate cancer, ovarian cancer, cervical cancer, bone cancer, spleen cancer, gall bladder cancer, brain cancer, pancreatic cancer, stomach cancer, anal cancer, multiple myeloma, post-transplant lymphoproliferative disease, restenosis, myelodysplastic syndrome, leukemia, or lymphoma.

6. A method of treating fibrosis by inhibiting signal transducer and activator of transcription 3 (STAT3) in an individual in need thereof, comprising administering to the individual an effective amount of a compound of claim 1, or a pharmaceutically acceptable salt or a solvate thereof.

7. The method of claim 6, wherein the fibrosis is pulmonary fibrosis, bone marrow fibrosis, intestine fibrosis, pancreatic fibrosis, joint fibrosis, liver fibrosis, retroperitoneum fibrosis, renal fibrosis, myelofibrosis, dermal fibrosis, or systemic sclerosis.

8. A method of treating an inflammatory disease or disorder by inhibiting signal transducer and activator of transcription 3 (STAT3) in an individual in need thereof, comprising administering to the individual an effective amount of a compound of claim 1, or a pharmaceutically acceptable salt or a solvate thereof.

9. The method of claim 8, wherein the inflammatory disease or disorder is inflammatory bowel disease, ulcerative colitis, psoriasis, uveitis, scleritis, multiple sclerosis, pancreatitis, or asthma.

10. A method of treating a neurodegenerative disease or disorder by inhibiting signal transducer and activator of transcription 3 (STAT3) in an individual in need thereof, comprising administering to the individual an effective amount of a compound of claim 1, or a pharmaceutically acceptable salt or a solvate thereof.

11. The method of claim 10, wherein the neurodegenerative disease or disorder is chemotherapy-induced peripheral neuropathy, diabetic neuropathy, or familial amyloid polyneuropathy.

12. A method of treating non-alcoholic fatty liver disease or steatohepatitis by inhibiting signal transducer and activator of transcription 3 (STAT3) in an individual in need thereof, comprising administering to the individual an effective amount of a compound of claim 1.

13. A method of treating cachexia by inhibiting signal transducer and activator of transcription 3 (STAT3) in an individual in need thereof, comprising administering to the individual an effective amount of a compound of claim 1, or a pharmaceutically acceptable salt or a solvate thereof.

14. A method of treating anaphylaxis by inhibiting signal transducer and activator of transcription 3 (STAT3) in an individual in need thereof, comprising administering to the individual and effective amount of a compound of claim 1, or a pharmaceutically acceptable salt or a solvate thereof.

* * * * *